(12) United States Patent
Thomas et al.

(10) Patent No.: US 9,023,661 B2
(45) Date of Patent: *May 5, 2015

(54) VISUAL GLUCOSE SENSOR AND METHODS OF USE THEREOF

(75) Inventors: Joseph Thomas, Raleigh, NC (US); Michael T. Cash, Timberlake, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1146 days.

This patent is subject to a terminal disclaimer.

(21) Appl. No.: 12/250,953

(22) Filed: Oct. 14, 2008

(65) Prior Publication Data

US 2009/0104714 A1  Apr. 23, 2009

Related U.S. Application Data

(60) Provisional application No. 60/981,011, filed on Oct. 18, 2007, provisional application No. 61/091,050, filed on Aug. 22, 2008.

(51) Int. Cl.
| | |
|---|---|
| *G01N 33/533* | (2006.01) |
| *G01N 33/53* | (2006.01) |
| *G01N 33/542* | (2006.01) |
| *G01N 33/66* | (2006.01) |
| *G01N 33/92* | (2006.01) |

(52) U.S. Cl.
CPC .............. *G01N 33/542* (2013.01); *G01N 33/66* (2013.01); *G01N 33/92* (2013.01)

(58) Field of Classification Search
CPC ...... G01N 33/582; G01N 33/53; A61K 8/498
See application file for complete search history.

(56) References Cited

U.S. PATENT DOCUMENTS

| | | | |
|---|---|---|---|
| 3,964,871 | A | 6/1976 | Hochstrasser |
| 4,981,779 | A | 1/1991 | Wagner |
| 5,001,054 | A | 3/1991 | Wagner |
| 5,246,867 | A | 9/1993 | Lakowicz et al. |
| 6,192,891 | B1 | 2/2001 | Gravel et al. |
| 6,277,627 | B1 | 8/2001 | Hellinga |
| D491,275 | S | 6/2004 | Walters et al. |
| 6,855,556 | B2 | 2/2005 | Amiss et al. |
| 6,922,576 | B2 | 7/2005 | Raskas |
| 7,064,103 | B2 | 6/2006 | Pitner et al. |
| D545,439 | S | 6/2007 | Draudt et al. |
| 7,563,891 | B2 * | 7/2009 | Pitner et al. .................. 544/105 |
| 2003/0165942 | A1 | 9/2003 | Czerney et al. |
| 2005/0014290 | A1 | 1/2005 | Hsieh et al. |
| 2005/0042704 | A1 | 2/2005 | Alarcon et al. |
| 2005/0113658 | A1 | 5/2005 | Jacobson et al. |
| 2005/0240119 | A1 | 10/2005 | Draudt et al. |
| 2006/0078908 | A1 | 4/2006 | Pitner et al. |
| 2006/0166368 | A1 | 7/2006 | Berkelman |
| 2006/0280652 | A1 | 12/2006 | Pitner et al. |
| 2008/0044856 | A1 | 2/2008 | Amiss et al. |
| 2008/0311675 | A1 | 12/2008 | Thomas et al. |

FOREIGN PATENT DOCUMENTS

| | | |
|---|---|---|
| EP | 1 318 177 A2 | 6/2003 |
| EP | 1 318 177 B1 | 6/2003 |
| JP | 2001-255330 | 9/2001 |
| WO | WO 03/057851 | 7/2003 |
| WO | WO 2006/025887 A2 * | 3/2006 .............. C09B 57/00 |

OTHER PUBLICATIONS

Lorimier et al. Construction of a fluorescent biosensor family. Protein Science 2002, vol. 11, pp. 2655-2675.*
Alexeev, V., et al., "Photonic Crystal Glucose-Sensing Material for Noninvasive Monitoring of Glucose in Tear Fluid," *Clinical Chemistry*, 2004, pp. 2353-2360, vol. 50, No. 12.
Long, J. et al., "Synthesis and Fluorescence Properties of Novel Benzo[α]phenoxazine-5-one Derivatives," *J. Heterocyclic Chem.*, 1999, pp. 895-899, vol. 36.
Richieri, G.V., et al., "A Fluorescently Labeled Intestinal Fatty Acid Binding Protein—Interactions with Fatty Acids and Its Use in Monitoring Free Fatty Acids," *J. Biol. Chem.*, 1992, pp. 23495-23501, vol. 267, No. 33.

* cited by examiner

*Primary Examiner* — Shafiqul Haq
(74) *Attorney, Agent, or Firm* — Alston & Bird LLP

(57) ABSTRACT

A method for determining the presence or amount of one or more ligands or analytes in a sample including contacting the sample with a biosensor having an environmentally-sensitive dye conjugated to a binding member, wherein the biosensor compound exhibits a detectable color change as a result of binding to the ligand or analyte or as a result of a change in concentration of the ligand or analyte in the sample. The presently disclosed biosensors can be used to detect the presence of or amount of physiologically-important metabolites, such as glucose, fatty acids, and lactate, in biological samples.

13 Claims, 7 Drawing Sheets

VISUAL GLUCOSE SENSOR AND METHODS OF USE THEREOF

CROSS-REFERENCE TO RELATED APPLICATIONS

This application is claims the benefit of U.S. Provisional Application Nos. 60/981,011, filed Oct. 18, 2007, and 61/091,050, filed Aug. 22, 2008, which are hereby incorporated herein in their entirety by reference.

FIELD OF THE INVENTION

The presently disclosed subject matter relates to biosensors including an environmentally-sensitive dye conjugated with a binding member having an affinity and specificity for one or more ligands or analytes and methods of their use for detecting one or more ligands or analytes, for example, one or more metabolites of interest, such as glucose, in a biological sample.

BACKGROUND

The detection of physiologically-important molecules, such as metabolites, in a biological sample can be critical for monitoring a condition or a disease state of a subject. For example, the monitoring of glucose can be used to diagnose and manage diabetes, where maintaining blood glucose within a normal range of 70 mg/dL to 120 mg/dL with insulin therapy and increased glucose monitoring can improve the long-term prognosis of subjects suffering from diabetes, including Type 1 and Type 2 diabetes. Glucose levels alone, however, often do not provide sufficient information for understanding the metabolic processes underlying diabetes and its development. The monitoring of other metabolites, such as fatty acids, can provide an additional understanding of the events leading to the development of a pre-diabetic state or insulin resistance in a subject suffering from diabetes, particularly Type 2 diabetes. Similarly, energy metabolites, such as lactate, a byproduct of moderate exercise, can be monitored to assess the energy expenditure, exercise burden, or fatigue level of a subject.

One method for detecting metabolites, such as glucose, fatty acids, and lactate, in a biological sample includes conjugating a fluorescent dye with a binding member, e.g., a binding protein, that has an affinity and specificity for a ligand or analyte, e.g., a metabolite of interest, and measuring a change in fluorescence upon ligand binding. Although fluorescence-based detection systems can be reliable, they can require sophisticated instrumentation and costs associated with such systems can be high. Thus, there is a need in the art for simple, cost-effective sensors for detecting metabolites, such as glucose, in biological samples. The presently disclosed subject matter addresses, in whole or in part, these and other needs in the art.

SUMMARY

The presently disclosed subject matter provides a biosensor compound including an environmentally-sensitive dye conjugated with a binding member, for example, a binding protein, such as a mutant glucose binding protein. The binding protein can undergo a conformational change upon binding to a ligand or analyte of interest. Without wishing to be bound to any one particular theory, this conformational change in the binding protein induces a change in environment of the dye that results in a change in the dye's electronic structure and the photophysical properties of the dye, which, in turn, translates to a change in color of the dye. Such biosensors can be used to detect and/or monitor the presence or amount of a metabolite of interest, such as glucose, in a biological sample.

Accordingly, in some embodiments, the presently disclosed subject matter provides a method for detecting one or more ligands or analytes, for example, one or more metabolites, such as glucose, in a biological sample. In some embodiments, the method includes: (a) providing a biosensor compound of Formula (I-IV):

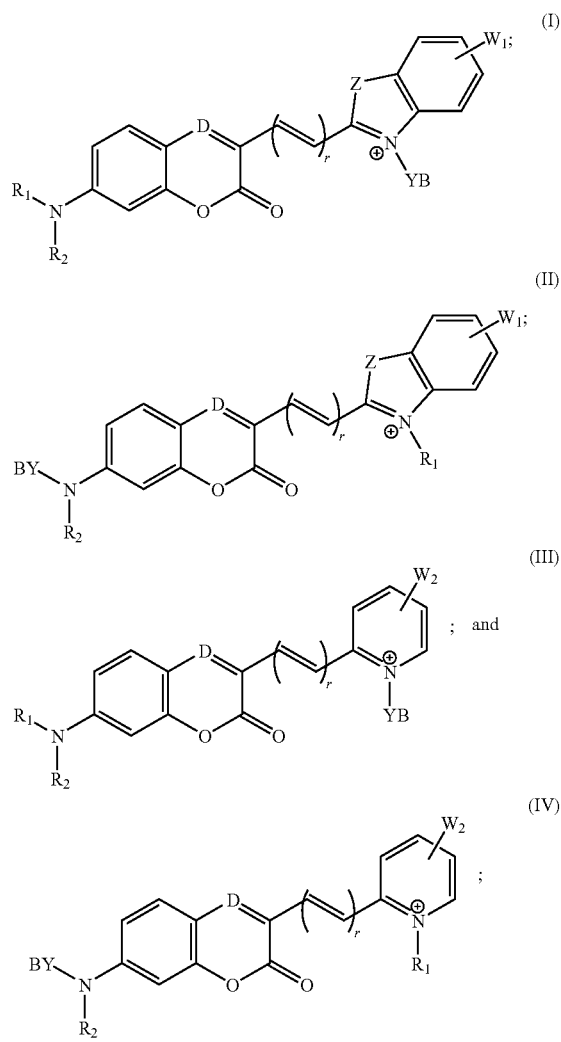

wherein:
r is an integer from 1 to 8;
D is CH or N;
$R_1$ and $R_2$ are each independently selected from the group consisting of alkyl, substituted alkyl, and $(CH_2)_sCO_2H$, wherein s is an integer from 2 to 5;
Z is selected from the group consisting of S, O, and $-CR_3R_4$, wherein $R_3$ and $R_4$ are each independently alkyl or substituted alkyl;
$W_1$ is selected from the group consisting of H, alkyl, substituted alkyl, $SO_3H$, fused benzene, and fused sulfobenzene;
$W_2$ is selected from the group consisting of H, alkyl, substituted alkyl, $SO_3H$, heteroalkyl, substituted heteroalkyl, cycloalkyl, substituted cycloalkyl, cycloheteroalkyl, substituted cycloheteroalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl;

Y—B is selected from the group consisting of:
—(CH$_2$)$_n$X$_1$C(=O)—(CH$_2$)$_m$—B,

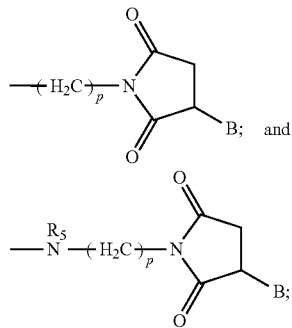

wherein:
m, n, and p are each independently an integer from 1 to 8;
X$_1$ is O or NR$_6$;
R$_5$ and R$_6$ are each independently selected from the group consisting of H, alkyl, substituted alkyl, heteroalkyl, substituted heteroalkyl, cycloalkyl, substituted cycloalkyl, cycloheteroalkyl, substituted cycloheteroalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; and
B is a binding member having a binding affinity for a ligand or analyte to be detected; and
wherein the biosensor compound exhibits a detectable color change as a result of binding to the ligand or analyte or as a result of a change in concentration of the ligand or analyte in the sample; (b) contacting the biosensor compound with a sample suspected of containing one or more ligands or analytes to bind the one or more ligands or analytes, if present, with the binding member, for example, a binding protein; and (c) detecting a color change to determine the presence or amount of the one or more ligands or analytes in the sample.

In certain embodiments, the presently disclosed biosensor compounds of Formula (I-IV) include an environmentally sensitive dye conjugated with a mutant glucose binding protein, for example, a mutant glucose binding protein having a mutation at W183C or SM4, as defined herein. In some embodiments, the observed color of the dye changes from magenta (e.g., an absorption wavelength of about 550 nm) to blue (e.g., an absorption wavelength of about 590 nm) in the presence of D-glucose. In other embodiments, the observed color of the dye changes from orange (e.g., an absorption wavelength of about 490 nm) to red (e.g., an absorption wavelength of about 520 nm) in the presence of D-glucose. Further, the glucose binding range of the presently disclosed biosensor compounds falls within the human physiological range of glucose (Kd=15 mM). Thus, the presently disclosed biosensor compounds are selective and specific for D-glucose, which allows the biosensor compounds to be used for detecting glucose in complex biological matrices.

The color change can be observed visually, e.g., with the naked eye, to indicate the presence of, e.g., to provide a qualitative determination of, a ligand or analyte of interest in a sample. Further, in some embodiments, the color change can be correlated with the concentration of the ligand or analyte in the sample using simple instrumentation, for example, an absorption detection device, such as a photometer, or in some embodiments, a color wheel, to provide a quantitative determination of the ligand or analyte in a sample. In some embodiments, the biosensor compounds exhibit a ratiometric response to one or more ligands or analytes. Further, in some embodiments, the presently disclosed sensor compounds can be immobilized on a solid matrix, for example, a chromatographic test strip, and included in a sensor device, such as a glucose sensor.

Accordingly, in some embodiments, the presently disclosed subject matter provides a biosensor device, e.g., a glucose sensor, comprising a biosensor compound of Formula (I-IV). In some embodiments, the presently disclosed subject matter provides a reagent for determining the presence or amount of one or more ligands or analytes in a sample, the reagent comprising a biosensor compound of Formula (I-IV). In some embodiments, the presently disclosed subject matter provides a kit for determining the presence or amount of one or more ligands or analytes in a sample, the kit comprising a biosensor compound of Formula (I-IV).

Certain aspects of the presently disclosed subject matter having been stated hereinabove, which are addressed in whole or in part by the presently disclosed subject matter, other aspects will become evident as the description proceeds when taken in connection with the accompanying Examples and Drawings as best described herein below.

BRIEF DESCRIPTION OF THE DRAWINGS

Figure 1:
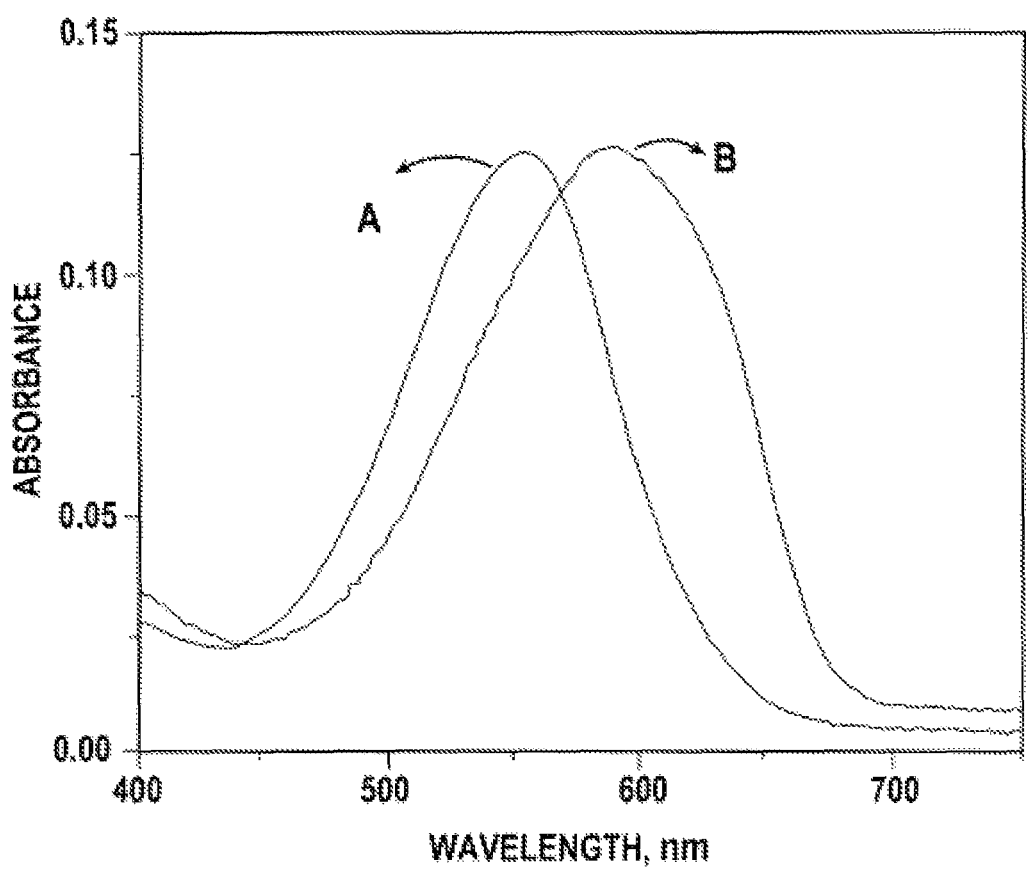
Figure 2:
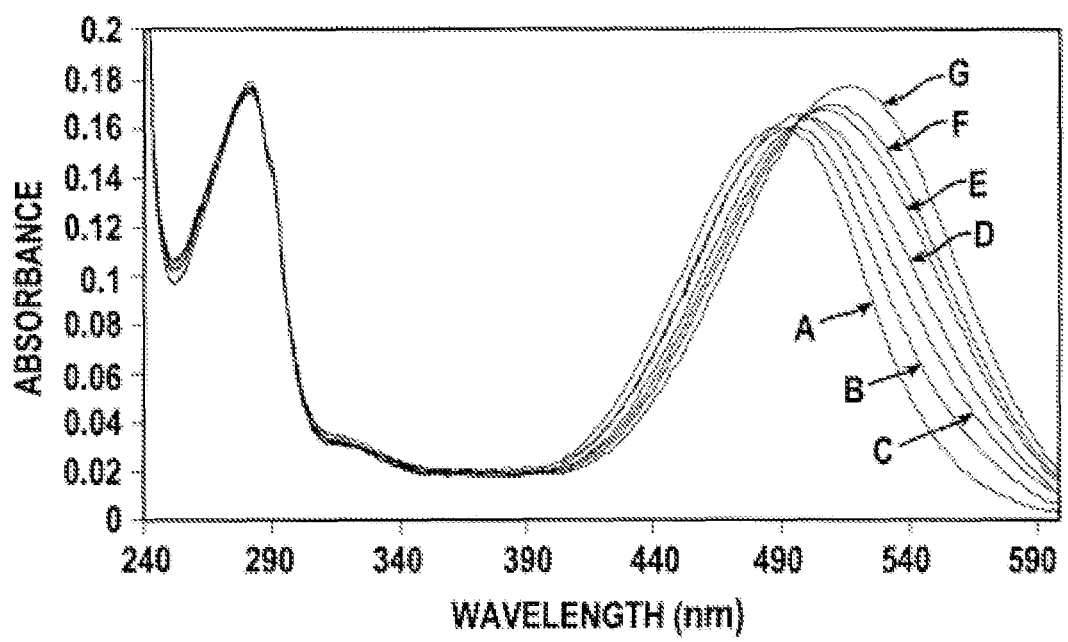
Figure 3:
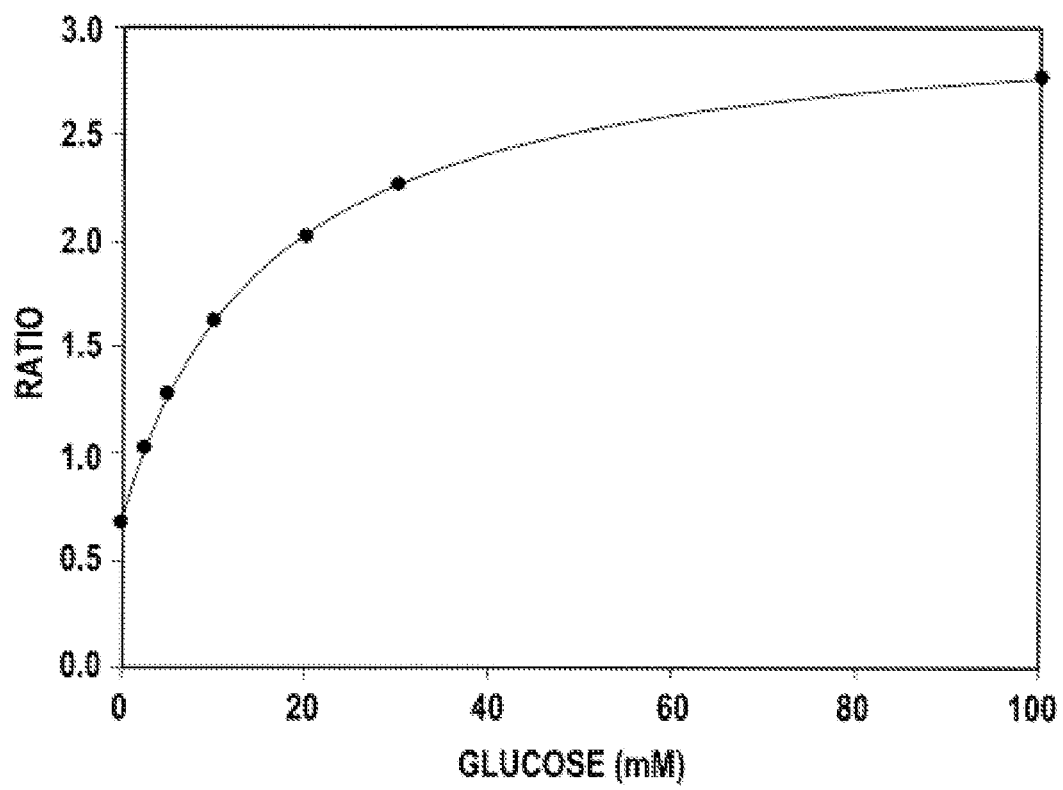

Having thus described the presently disclosed subject matter in general terms, reference will now be made to the accompanying Drawings, which are not necessarily drawn to scale, and wherein:

FIG. 1 shows representative absorption spectra of a presently disclosed biosensor compound of Formula (Ia) conjugated with a mutated glucose/galactose binding protein having a cysteine substituted for tryptophan at position 183 (W183C) before (A) and after (B) the addition of glucose;

FIG. 2 shows a change in representative absorption spectra of a biosensor compound of Formula (IIIa), e.g., SM4-o-ICOPIC, with increasing glucose concentration over the glucose concentration range of about 0 mM to about 100 mM. A=0 mM glucose, B=2.5 mM glucose, C=5 mM glucose, D=10 mM glucose, E=20 mM glucose, F=30 mM glucose, and G=100 mM glucose;

FIG. 3 shows a representative ratiometric glucose binding curve obtained from absorption spectra of a biosensor compound of Formula (IIIa), e.g., SM4-o-ICOPIC, over glucose concentrations ranging from about 0 mM to about 100 mM as provided in FIG. 2 immediately hereinabove;

FIGS. 4A-4D demonstrate the effect of excitation wavelength on the fluorescence spectra of a biosensor compound of Formula (IIIa), e.g., SM4-o-ICOPIC, over glucose concentrations ranging from about 0 mM to about 100 mM.

Figure 4A:
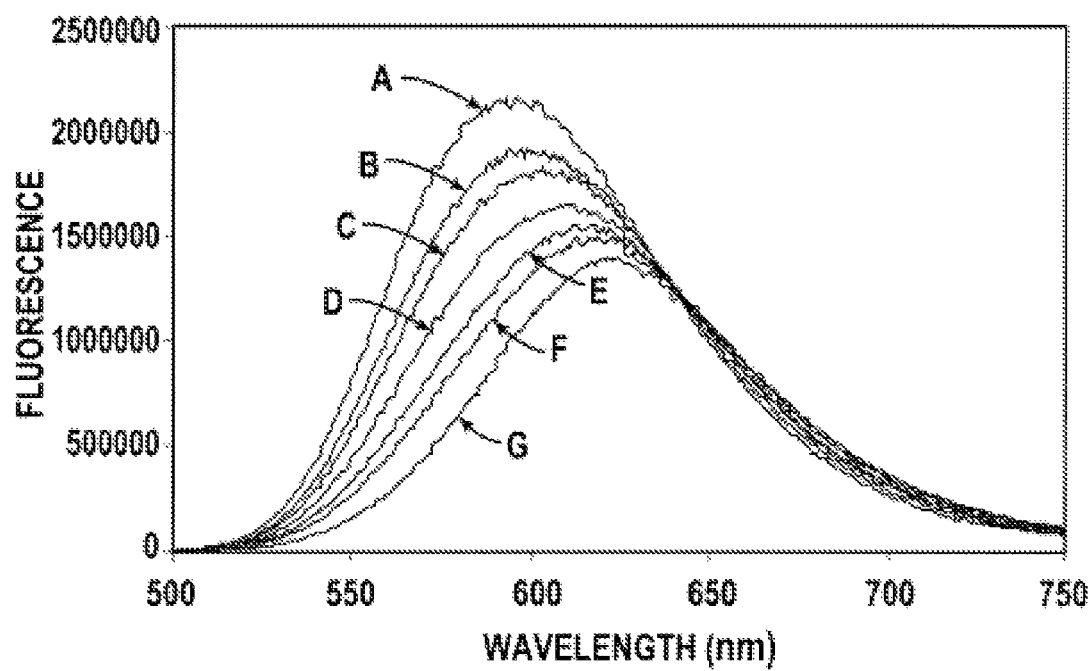
Figure 4B:
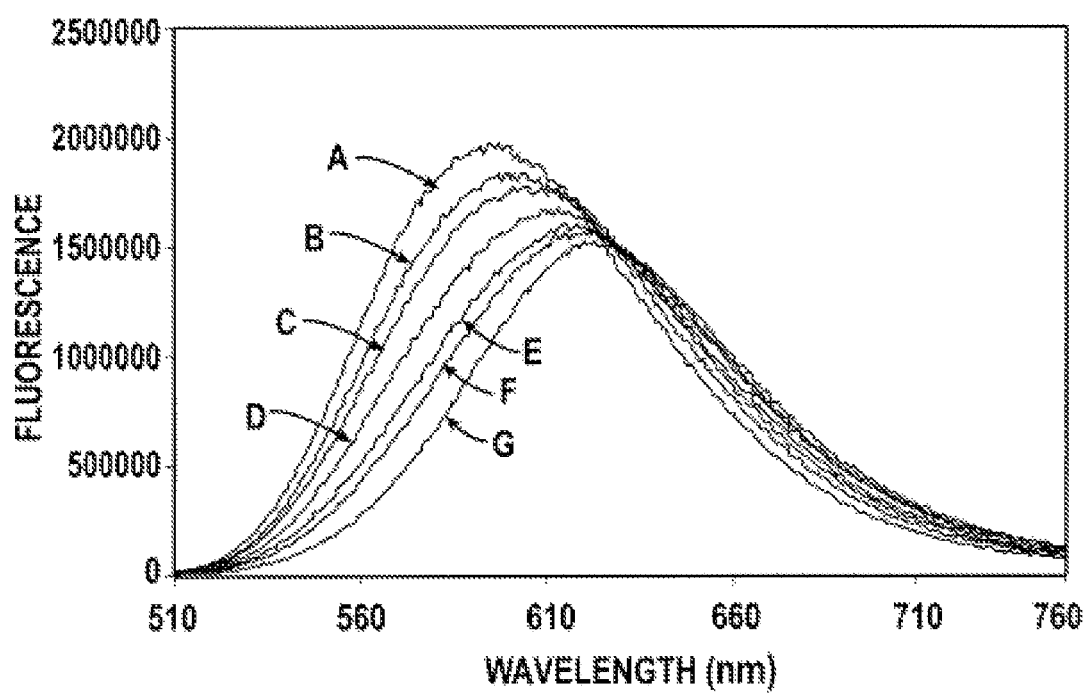
Figure 4C:
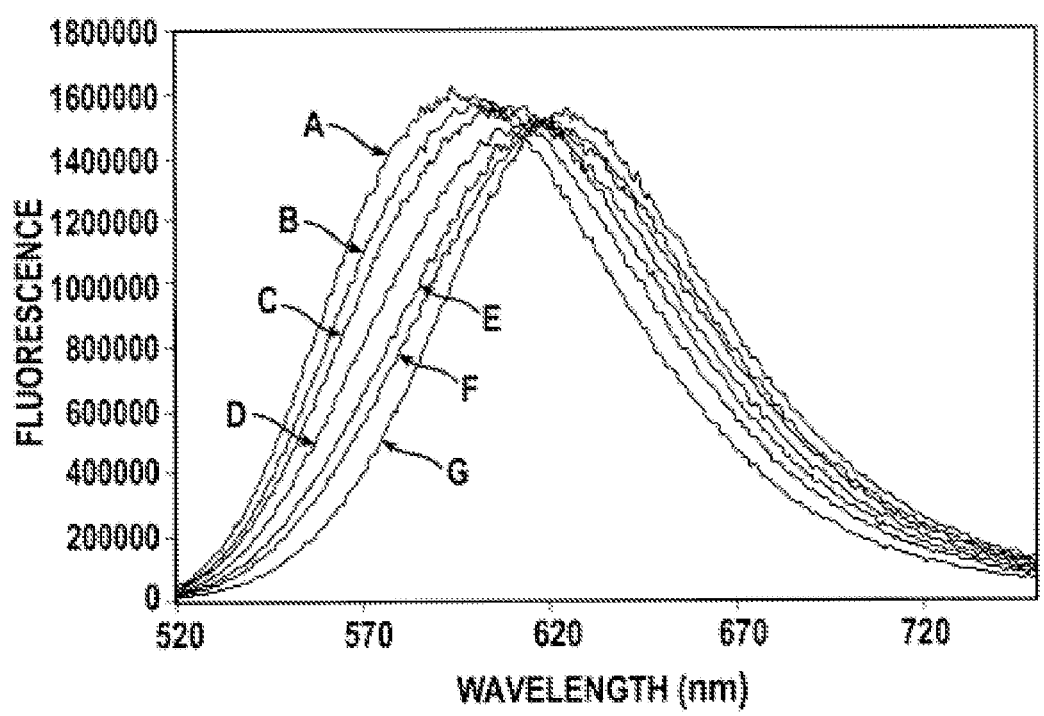
Figure 4D:
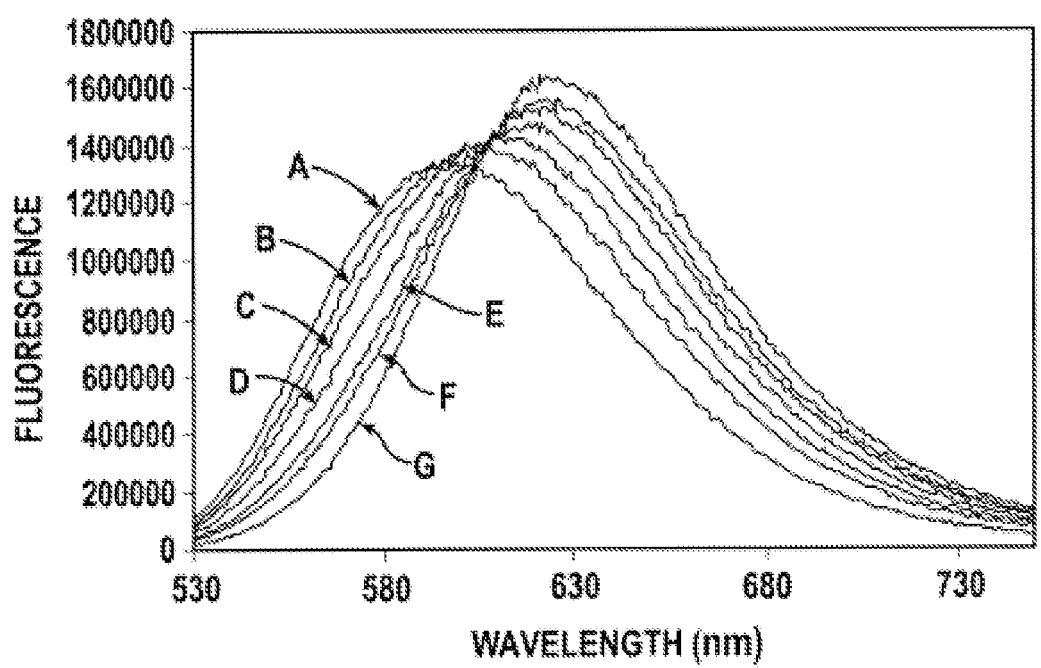

FIG. 4A shows a series of fluorescence spectra of a biosensor compound of Formula (IIIa), e.g., SM4-o-ICOPIC, exited at 485 nm. A=0 mM glucose, B=2.5 mM glucose, C=5 mM glucose, D=10 mM glucose, E=20 mM glucose, F=30 mM glucose, and G=100 mM glucose;

FIG. 4B shows a series of fluorescence spectra of a biosensor compound of Formula (IIIa), e.g., SM4-o-ICOPIC, exited at 495 nm. A=0 mM glucose, B=2.5 mM, C=5 mM, D=10 mM glucose, E=20 mM glucose, F=30 mM glucose, and G 100 mM glucose;

FIG. 4C shows a series of fluorescence spectra of a biosensor compound of Formula (IIIa), e.g., SM4-o-ICOPIC, exited at 505 nm. A=0 mM glucose, B=2.5 mM glucose, C=5 mM glucose, D=10 mM glucose, E=20 mM glucose, F=30 mM glucose, and G=100 mM glucose;

FIG. 4D shows a series of fluorescence spectra of a biosensor compound of Formula (IIIa), e.g., SM4-o-ICOPIC, exited at 515 nm. A=0 mM glucose, B=2.5 mM glucose, C=5 mM glucose, D=10 mM glucose, E=20 mM glucose, F=30 mM glucose, and G=100 mM glucose;

DETAILED DESCRIPTION

The presently disclosed subject matter now will be described more fully hereinafter with reference to the accompanying Drawings, in which some, but not all embodiments of the presently disclosed subject matter are shown. Many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims. Although specific terms are employed herein, they are used in a generic and descriptive sense only and not for purposes of limitation.

The terms "a," "an," and "the" refer to "one or more" when used in this application, including the claims. Thus, for example, reference to "a sample" includes a plurality of samples, unless the context clearly is to the contrary (e.g., a plurality of samples), and so forth.

Throughout this specification and the claims, the words "comprise," "comprises," and "comprising" are used in a non-exclusive sense, except where the context requires otherwise.

As used herein, the term "about," when referring to a value is meant to encompass variations of, in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

I. Biosensor Compounds of Formula (I-IV)

Designing a biosensor system that exhibits a color change in physiologically relevant ranges of target ligands or analytes, such as glucose, requires consideration of the dye, dye-protein linker, protein, and protein conjugation site. The presently disclosed subject matter includes biosensor compounds that have an absorption wavelength in the visible spectral region. As used herein, the terms "biosensor" and "biosensor compound" generally refer to a device or compound that undergoes a detectable change in specific response to the presence of a ligand or analyte. Such biosensors combine the molecular recognition properties of biological macromolecules, such as a binding protein, with environmentally-sensitive dyes that produce a detectable color change upon ligand or analyte binding. The detectable color change can include a shift in the absorption wavelength, a change in intensity, or a combination thereof. Accordingly, a biosensor translates a binding event into a directly measurable photometric or calorimetric property.

More particularly, in some embodiments, the presently disclosed subject matter provides a biosensor compound of Formula (I-IV):

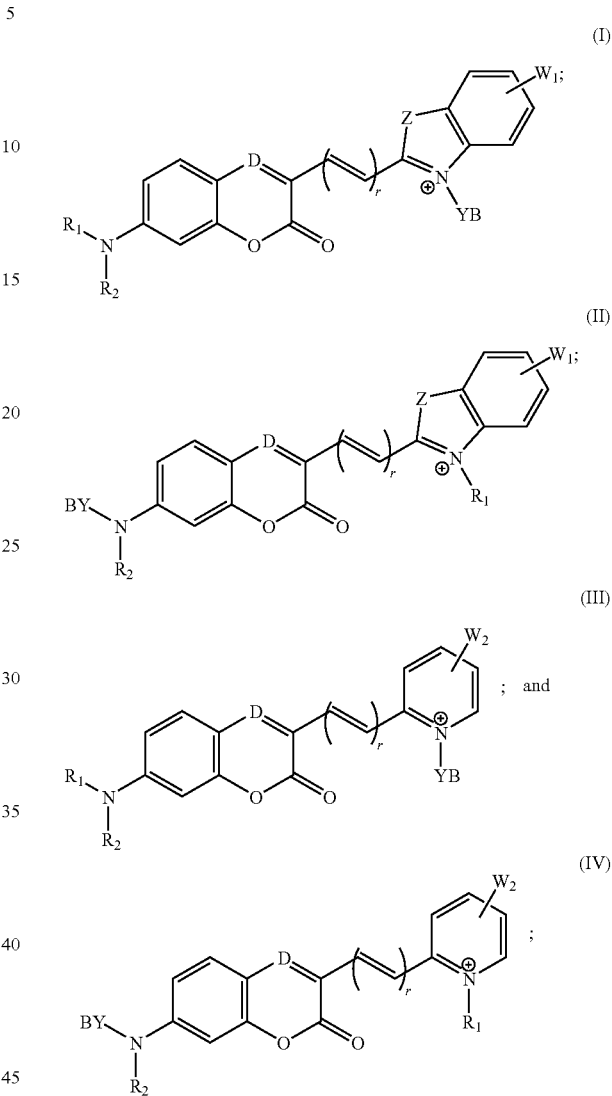

wherein:

r is an integer from 1 to 8;

D is CH or N;

$R_1$ and $R_2$ are each independently selected from the group consisting of alkyl, substituted alkyl, and $(CH_2)_sCO_2H$, wherein s is an integer from 2 to 5;

Z is selected from the group consisting of S, O, and $—CR_3R_4$, wherein $R_3$ and $R_4$ are each independently alkyl or substituted alkyl;

$W_1$ is selected from the group consisting of H, alkyl, substituted alkyl, $SO_3H$, fused benzene, and fused sulfobenzene;

$W_2$ is selected from the group consisting of H, alkyl, substituted alkyl, $SO_3H$, heteroalkyl, substituted heteroalkyl, cycloalkyl, substituted cycloalkyl, cycloheteroalkyl, substituted cycloheteroalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl;

Y—B is selected from the group consisting of:
—(CH$_2$)$_n$X$_1$C(=O)—(CH$_2$)$_m$—B,

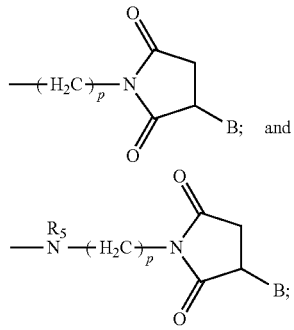

wherein:
m, n, and p are each independently an integer from 1 to 8;
X$_1$ is O or NR$_6$;
R$_5$ and R$_6$ are each independently selected from the group consisting of H, alkyl, substituted alkyl, heteroalkyl, substituted heteroalkyl, cycloalkyl, substituted cycloalkyl, cycloheteroalkyl, substituted cycloheteroalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; and B is a binding member having a binding affinity for a ligand or analyte to be detected; and wherein the biosensor compound exhibits a detectable color change as a result of binding to the ligand or analyte or as a result of a change in concentration of the ligand or analyte in the sample.

In some embodiments, the biosensor compound has a structure selected from the group consisting of:

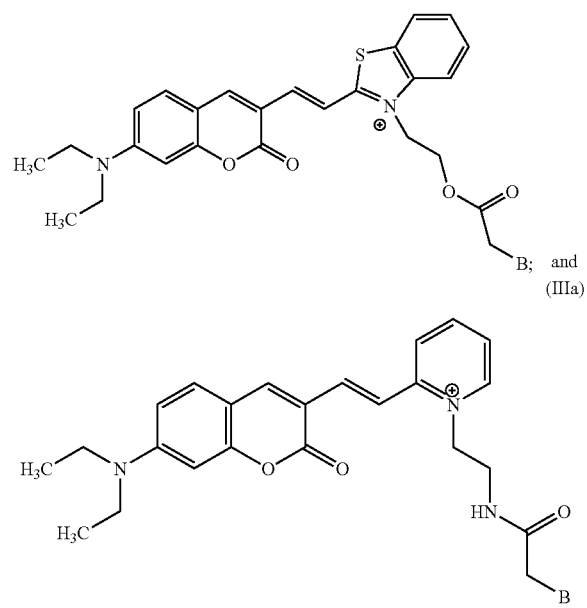

wherein B is as defined hereinabove.

In some embodiments, the presently disclosed biosensor compounds of Formula (I-IV) include a coumarin nucleus or a derivative of a coumarin nucleus. Suitable nuclei and methods for preparing coumarin nucleus derivatives are described in U.S. Patent Application Publication No. 2006/0280652, filed May 18, 2005, which is incorporated by reference in its entirety. As used herein, a "derivative of a coumarin nucleus" refers to a chemical compound that is derived from or obtained from a parent compound, e.g., coumarin, and contains essential elements of the parent compound but typically includes one or more different functional groups. Such functional groups can be added to a parent compound, for example, to improve the molecule's solubility, absorption, biological half life, spectrometric or calorimetric properties, and the like, or to decrease the toxicity of the molecule, eliminate or attenuate any undesirable side effect of the molecule, and the like.

A derivative of a coumarin nucleus is meant to include any chemical modification, addition, deletion, or substitution to a coumarin nucleus. Further, a derivative of a coumarin nucleus can include any reaction product of the derivative, for example, the reaction product of the derivative with an amino acid residue. Accordingly, in some embodiments, the presently disclosed biosensor compound can include a coumarin nucleus having a reactive group that can be conjugated, e.g., covalently attached, to an amino acid, for example, an amino acid residue of a protein. A non-limiting example of a derivative of coumarin is an ester or amide of a coumarin nucleus having a carboxylic acid functional group.

More particularly, in some embodiments, the coumarin nucleus can include a thiol-reactive group that can be conjugated to the thiol moiety of a cysteine amino acid residue in a natural or an engineered or mutated protein. As used herein, the term "thiol-reactive group" refers to a substituent group that can react with a thiol moiety to form a carbon-sulfur bond. Examples of suitable thiol-reactive groups that can be introduced into the presently disclosed biosensor compounds include a halo-acetyl group and a halo-acetamide group. In some embodiments, the halo-acetyl group includes an iodoacetyl group, whereas the halo-acetamide group can include an iodoacetamide or bromoacetamide group. One of ordinary skill in the art upon review of the presently disclosed subject matter would recognize that other thiol-reactive groups known in the art, such as maleimide groups, are suitable for use with the presently disclosed subject matter.

As described immediately herein below, the presently disclosed biosensor compounds of Formula (I-IV) comprise, e.g., are conjugated with, a binding member of a specific binding pair, such as a binding protein, to form a biosensor compound that can be used to detect one or more analytes in a sample under test. Suitable binding proteins are described in U.S. Patent Application Publication No. 2006/0280652, filed May 18, 2005, which is incorporated by reference in its entirety.

As used herein, the term "conjugate" refers to a molecule comprising two or more subunits bound together, optionally through a linking group, to form a single molecular structure. The binding can be made either by a direct chemical bond between the subunits or through a linking group. Such binding in a conjugate typically is irreversible.

As used herein, the term "affinity" refers to the strength of the attraction between one binding member of a specific binding pair to another binding member of a specific binding pair at a particular binding site. The term "specificity" and derivations thereof, refer to the likelihood that a binding member will bind to another member of a specific binding pair. Such binding between one binding member, e.g., a binding protein, to another binding member of a specific binding pair, e.g., a ligand or analyte, can be reversible.

As used herein, the term "binding protein" refers to a protein, that when conjugated with an environmentally-sensitive dye, interacts with a specific analyte or ligand in a manner capable of producing a detectable signal differentiable from when a target analyte or ligand is present or absent, or when a target analyte or ligand is present in varying concentrations over time. The term "producing a detectable signal" refers to the ability to recognize a change in a property of a reporter group, e.g., a dye, in a manner that enables the detection of ligand-protein binding. Further, the producing of a detectable signal can be reversible or non-reversible. The signal-producing event includes continuous, programmed, and episodic means, including one-time or reusable applications. The reversible signal-producing event can be instantaneous or can be time-dependent, so long as a correlation with the presence or concentration of analyte is established.

In some embodiments, the binding member includes a glucose/galactose binding protein (GGBP), a fatty acid binding protein (FABP), or a GGBP derivative. In one embodiment of the presently disclosed subject matter, a mutated glucose/galactose binding protein, such as W183C, SM4, or Y10C (defined infra) comprises a detectable reporter group, e.g., a coumarin-based dye as represented in Formula I-IV, whose detectable characteristics alter upon glucose binding. In some embodiments, the FABP is an intestinal fatty acid binding protein (I-FABP).

The change in the detectable characteristics can be due to an alteration in the environment of the dye attached to the mutated GGBP or to a conformational change of the protein resulting from binding. Without wishing to be bound to any one particular theory, the binding protein comprising the biosensor can adopt two conformations: a ligand-free open form and a closed form when bound to a ligand. These two conformations can interconvert, for example, via a global hinge-binding mechanism upon ligand binding or changes in ligand concentration. By positioning environmentally-sensitive dyes in locations that undergo local conformational changes in concert with these global conformational changes, such ligand-mediated conformational changes can be exploited to couple ligand binding to a color change. Accordingly, these engineered conformational coupling mechanisms enable reagentless optical biosensors to be formed from selected binding proteins and environmentally-sensitive dyes. Exemplary mutations of binding proteins are described in U.S. Pat. No. 7,064,103 to Pitner et al., issued Jun. 20, 2006, U.S. Pat. No. 6,855,556 to Amiss et al., issued Feb. 15, 2005, and U.S. Patent Application Publication No. 2006/0280652, filed May 18, 2005, each of which is incorporated by reference in its entirety.

Particular examples of mutations of a GGBP protein (for example the *E. coli.* GGBP having the amino acid sequence accessible in the database for The National Center for Biotechnology Information (NCBI) as GenBank Accession No. 2GBP, the entire record of which is incorporated by reference) include, but are not limited to, a GGBP protein having a cysteine substituted for tyrosine at position 10 (Y10C), a cysteine substituted for tryptophan at position 183 (W183C), a mutated GGBP having the following substitutions: N39I, G82E, Q83K, N84D, Q175E, Q177H, L178M, W183C, N259E and N260S (referred to as "SM4"), and other mutated GGBPs disclosed in copending U.S. application Ser. No. 11/738,442, filed Apr. 20, 2007, and published as U.S. Patent Publication No. 2008-0044856, which is incorporated herein by reference in its entirety. Accordingly, in some embodiments, the binding protein is selected from the group consisting of W183C, SM4, and Y10C.

The mutation can serve one or more of several purposes. For example, a naturally occurring protein can be mutated to change the long-term stability, including thermal stability, of the protein, to conjugate the protein to a particular encapsulation matrix or polymer, to provide binding sites for detectable reporter groups, to adjust its binding constant with respect to a particular analyte, or combinations thereof.

The target analyte or ligand of interest and the mutated protein can act as binding partners. The term "associates" or "binds" as used herein refers to binding partners having a relative binding constant (Kd) sufficiently strong to allow detection of binding to the protein by a detection means. The Kd can be calculated as the concentration of free analyte at which half the protein is bound, or vice versa. When the analyte of interest is glucose, the Kd values for the binding partners are between about 0.0001 mM and about 50 mM.

In addition to changing binding characteristics, derivative polypeptides or proteins also can be used to incorporate a presently disclosed dye onto or within the binding member. The dyes can be used to indicate a change in the binding member, including, but not limited to, three-dimensional conformational changes, changes in orientation of the amino acid side chains of proteinaceous binding domains, and redox states of the binding member. With the addition/substitution of one or more residues into the primary structure of a protein, some of the labeling moieties used in the current methods and compositions can be attached through chemical means, such as reduction, oxidation, conjugation, and condensation reactions. Examples of residues commonly used to label proteins include, but are not limited to, lysine and cysteine. For example, any thiol-reactive group can be used to attach a dye to a naturally occurring or engineered cysteine in the primary structure of the polypeptide. Also, for example, lysine residues can be labeled using succinimide ester derivatives of dyes. See Richieri G. V. et al., *J. Biol. Chem.*, 267: 23495-501 (1992), which is incorporated herein by reference.

An environmentally-sensitive dye, e.g., a dye having a coumarin nucleus, such as the dyes comprising the presently disclosed biosensor compounds of Formula (I-IV), or a derivative thereof, can be covalently attached to a binding protein in a site-specific manner to obtain the desired color change. The dye can be attached at a site on the binding protein so that the conformational change maximizes the color change. Conjugates containing dyes attached at various sites, for example, cysteine mutant sites constructed in mutated GGBPs, can be screened to identify which sites result in the largest color change upon glucose binding.

II.B Methods of Detecting the Presence or Amount of an Analyte

Biosensor compounds of Formula (I-IV) can be used in combination with binding protein assays to detect physiologically important molecules, including metabolites, such as glucose, fatty acids, and lactates, in biological samples. Accordingly, the presently disclosed biosensor compounds of Formula (I-IV) include a reactive group that can be used to couple or conjugate the dye with another molecule, including a member of a specific binding pair, such as a binding protein or a receptor, which has an affinity for a specific ligand or analyte.

In some embodiments, the presently disclosed subject matter provides a method for determining the presence or amount of one or more ligands or analytes in a sample, the method comprising:

(a) providing a biosensor compound of Formula (I-IV):

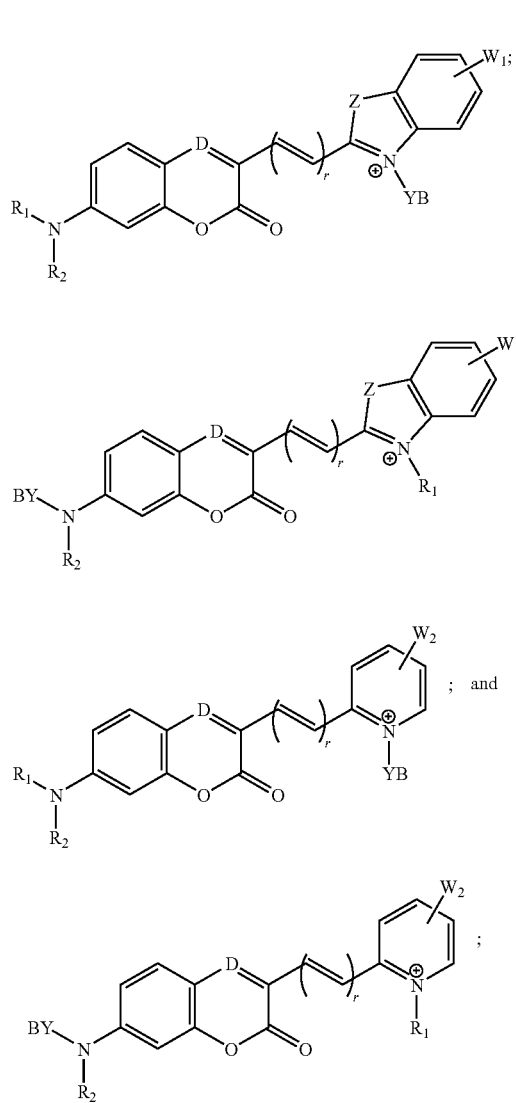

wherein:
r is an integer from 1 to 8;
D is CH or N;
$R_1$ and $R_2$ are each independently selected from the group consisting of alkyl, substituted alkyl, and $(CH_2)_sCO_2H$, wherein s is an integer from 2 to 5;
Z is selected from the group consisting of S, O, and $-CR_3R_4$, wherein $R_3$ and $R_4$ are each independently alkyl or substituted alkyl;
$W_1$ is selected from the group consisting of H, alkyl, substituted alkyl, $SO_3H$, fused benzene, and fused sulfobenzene;
$W_2$ is selected from the group consisting of H, alkyl, substituted alkyl, $SO_3H$, heteroalkyl, substituted heteroalkyl, cycloalkyl, substituted cycloalkyl, cycloheteroalkyl, substituted cycloheteroalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl;

Y—B is selected from the group consisting of:
$-(CH_2)_nX_1C(=O)-(CH_2)_m-B$,

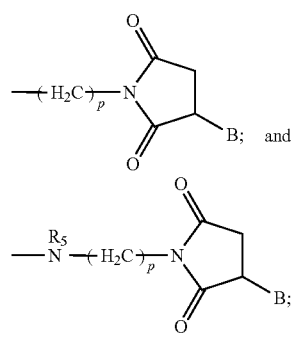

wherein:
m, n, and p are each independently an integer from 1 to 8;
$X_1$ is O or $NR_6$;
$R_5$ and $R_6$ are each independently selected from the group consisting of H, alkyl, substituted alkyl, heteroalkyl, substituted heteroalkyl, cycloalkyl, substituted cycloalkyl, cycloheteroalkyl, substituted cycloheteroalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; and
B is a binding member having a binding affinity for a ligand or analyte to be detected; and
wherein the biosensor compound exhibits a detectable color change as a result of binding to the ligand or analyte or as a result of a change in concentration of the ligand or analyte in the sample;
(b) contacting the biosensor compound with a sample suspected of containing one or more ligands or analytes to bind the one or more ligands or analytes, if present, to the binding member; and
(c) detecting a color change to determine the presence or amount of one or more ligands or analytes in the sample.

Embodiments that exhibit a shift in absorption wavelength upon ligand binding allow a biosensor comprising a presently disclosed biosensor compound of Formula (I-IV) to be self-referencing. In such embodiments, the biosensor compound exhibits an increase in a first absorption wavelength in the presence of a metabolite, such as glucose, and a decrease in a second absorption wavelength. A ratio between the first absorption wavelength and the second absorption wavelength can be calculated to determine the concentration of glucose in the sample under test. Such self referencing can correct for variations in the biosensor, such as variations caused by noise or instability, without requiring a reference dye. Such wavelengths can be used to observe a ratiometric response in the output of the biosensor. As used herein, the term "ratiometric response" means that the intensities of the first absorption wavelength and the second absorption wavelength vary independently such that the ratio of the two absorption wavelengths (the "ratiometric quotient") can be used to indicate the presence and/or amount, e.g., concentration, of the ligand or analyte in the sample.

Accordingly, in some embodiments, the presently disclosed method further comprises: (a) measuring an absorption intensity at a first absorption wavelength before contacting the biosensor compound with the sample suspected of containing one or more ligands or analytes; (b) measuring an absorption intensity at a second absorption wavelength after contacting the biosensor compound with the sample suspected of containing one or more ligands or analytes; and (c) determining a ratio of the second absorption wavelength to the first absorption wavelength to determine the presence or amount of one or more ligands or analytes in the sample.

The binding of the one or more target ligands or analytes to a biosensor compound comprising a binding member induces a discernable color change in the environmentally-sensitive dye of the biosensor compound. Discernable color changes include, but are not limited to, an absorption wavelength shift and/or change, e.g., an increase or decrease, in signal intensity. In some embodiments, the biosensor compound generates a signal, for example, a first absorption wavelength, even when not bound to a target analyte. In such embodiments, the binding of the target analyte can result in a color change, such that binding is discernable. The binding of the biosensor compound to a target ligand or analyte also can cause an increase or decrease in signal intensity.

A detected color change due to either a conformational change in the binding member, e.g., a binding protein, subsequent changes in the microenvironment of the dye, or both, can be correlated to the presence and/or amount, i.e., analyte concentration, of one or more target ligands or analytes. In some embodiments of the presently disclosed method, the binding protein undergoes a conformation change as a result of changes in ligand or analyte concentration of the sample suspected of containing one or more ligands or analytes. Accordingly, the method detects a color change as a result of changes in the ligand or analyte concentration. Such colors changes can provide a visually distinguishable color gradient over various glucose concentrations. The presently disclosed methods, for example, can exhibit a dynamic range of about 5 mg/dL to about 100 mg/dL, although methods exhibiting a broader or a narrower dynamic range are within the scope of the presently disclosed subject matter.

In some embodiments, the observed color of the dye changes from magenta (e.g., an absorption wavelength of about 550 nm) to blue (e.g., an absorption wavelength of about 590 nm) in the presence of D-glucose. In other embodiments, the observed color of the dye changes from orange (e.g., an absorption wavelength of about 490 nm) to red (e.g., an absorption wavelength of about 520 nm) in the presence of D-glucose. The color change can be observed with the naked eye to indicate the presence of, e.g., to provide a qualitative determination of, a ligand or analyte of interest in a sample. Further, in some embodiments, the color change can be correlated with the concentration of the ligand or analyte in the sample using simple instrumentation, for example, an absorption detection device, such as a photometer, or in some embodiments, a color wheel, to provide a quantitative determination of the ligand or analyte, e.g., glucose, in a sample.

The amount of one or more ligands or analytes present in a sample under test can be represented as a concentration. As used herein, the term "concentration" has its ordinary meaning in the art. The concentration can be expressed as a qualitative value, such as negative- or positive-type results, for example, as a "YES" or "NO" response indicating the presence or absence of a target analyte, or as a quantitative value, for example in units of mg/dL. Further, the concentration of a given analyte can be reported as a relative quantity or an absolute quantity. As used herein, "quantitative results" refer to results that provide absolute or relative values.

The quantity (concentration) of a ligand or analyte can be equal to zero, indicating the absence of a particular ligand or analyte sought or that the concentration of the particular ligand or analyte is below the detection limits of the biosensor. The quantity measured can be the measured signal, e.g., a color change, without any additional measurements or manipulations. Alternatively, the quantity measured can be expressed as a difference, percentage or ratio of the measured value of the particular analyte to a measured value of another compound including, but not limited to, a standard or another ligand or analyte. The difference can be negative, indicating a decrease in the amount of measured ligand(s) or analyte(s). The quantities also can be expressed as a difference or ratio of the ligand(s) or analyte(s) to itself, measured at a different point in time. The quantities of ligands or analytes can be determined directly from a generated signal, or the generated signal can be used in an algorithm, with the algorithm designed to correlate the value of the generated signals to the quantity of ligands(s) or analyte(s) in the sample.

The detection of the color change can be carried out continuously or intermittently at predetermined times allowing episodic or continuous sensing of an analyte, for example, glucose, to be performed. Thus, the presently disclosed biosensor compounds are amenable for use with devices capable of continuously measuring the concentrations of one or more analytes.

Accordingly, in some embodiments, the method further comprises continuously: (a) contacting the biosensor compound with the sample suspected of containing one or more ligands or analytes; and (b) detecting the color change. As used herein, the term "continuously," in conjunction with the measuring of a ligand or analyte, means the biosensor either generates or is capable of generating a detectable signal at any time during the life span of the biosensor. The detectable signal can be constant, in that the biosensor is always generating a signal, even if a signal is not detected. Alternatively, the biosensor can be used episodically, such that a detectable signal can be generated, and detected, at any desired time.

As provided hereinabove, the presently disclosed methods include biosensor compounds including environmentally-sensitive dyes conjugated with specific binding partners for a particular analyte or analytes of interest. A specific binding partner or member, as used herein, is a member of a specific binding pair. A "specific binding pair" refers to two different molecules where one of the molecules through chemical or physical means specifically binds the second molecule. In this sense, an analyte is a reciprocal member of a specific binding pair. Further, specific binding pairs can include members that are analogs of the original specific binding partners, for example, an analyte-analog having a similar structure to the analyte. By "similar" it is intended that, for example, an analyte-analog has an amino acid sequence that has at least about 60% or 65% sequence identity, about 70% or 75% sequence identity, about 80% or 85% sequence identity, about 90%, 91%, 92%, 93%, 94%, 95%, 96%, 97%, 98%, 99% or greater amino acid sequence identity compared to an analyte amino acid sequence using alignment programs and standard parameters well known in the art. An analog of an analyte also can have the same function as an analyte.

The term "analyte," as used herein, generally refers to a substance to be detected, which can be present or suspected of being present in a test sample. More particularly, an "analyte" can be any substance for which there exists a naturally occurring specific binder partner, such as a binding protein or receptor, or for which a specific binding partner can be prepared. Accordingly, an "analyte" is a substance that can bind one or more specific binding partners in an assay. In some embodiments, the analyte can be any compound, such as a metabolite, to be detected or measured and which has at least one binding site.

In some embodiments, the analyte is a ligand. As used herein, the term "ligand" refers to any molecule capable of binding to the binding member, e.g., a binding protein, via an active site. In some embodiments, the ligand is a protein, a peptide or hapten antigen, such as a bacterial antigen, or a hormone, a cytokine, an interleukin, a tumor necrosis factor (TNF) a growth factor, a viral protein, or a peptide or nucleotide sequence. As used herein, the term "active site" refers to amino acid residues of the binding member that contribute to the binding of the ligand. This active site also can be referred to as a "binding site" or "paratope."

The target analyte or ligand can be any molecule or compound, of which the presence or amount is to be determined in a sample under test. Examples of classes of analytes that can be measured by the presently disclosed methods include, but are not limited to carbohydrates, fatty acids, lactate or lactic acid, amino acids, peptides, polypeptides, proteins, lipids, nucleotides, oligonucleotides, polynucleotides, glycoproteins or proteoglycans, lipoproteins, lipopolysaccharides, drugs, drug metabolites, small organic molecules, inorganic molecules and natural or synthetic polymers. Examples of target analytes include, but are not limited to, glucose, free fatty acids, lactate or lactic acid, C-reactive protein and anti-inflammatory mediators, such as cytokines, eicosanoids, or leukotrienes. In some embodiments, the target analytes are selected from the group consisting of fatty acids, C-reactive protein, and leukotrienes. In another embodiment, the target analytes are selected from the group consisting of glucose, lactate or lactic acid and fatty acids.

As used herein, the term "carbohydrate" includes, but is not limited to monosaccharides, such as glucose, disaccharides, oligosaccharides and polysaccharides. "Carbohydrate" also includes, but is not limited to, molecules comprising carbon, hydrogen and oxygen that do not fall within the traditional definition of a saccharide, i.e., an aldehyde or ketone derivative of a straight chain polyhydroxyl alcohol, containing at least three carbon atoms. Thus, for example, a carbohydrate as used herein can contain fewer than three carbon atoms.

The term "fatty acids," as used herein include all fatty acids, including free fatty acids (FFA) and fatty acids esterified to other molecules. Examples of specific fatty acids include, but are not limited to, palmitate, stearate, oleate, linoleate, linolenate, and arachidonate. The term "free fatty acid" is used herein as it is known in the art in that FFA are not part of other molecules, such as triglycerides or phospholipids. Free fatty acids also include non-esterified fatty acids that are bound to or adsorbed onto albumin. As used herein, the term "unbound free fatty acid" (unbound FFA) is used to denote a free fatty acid or free fatty acids that are not bound or adsorbed onto albumin or other serum proteins.

As used herein, the term "lipid" is used as it is in the art, i.e., a substance of biological origin that is made up primarily or exclusively of nonpolar chemical groups such that it is readily soluble in most organic solvents, but only sparingly soluble in aqueous solvents. Examples of lipids include, but are not limited to, fatty acids, triacylglycerols, glycerophospholipids, sphingolipids, cholesterol, steroids and derivatives thereof. For example, "lipids" include but are not limited to, the ceramides, which are derivatives of sphingolipids and derivatives of ceramides, such as sphingomyelins, cerebrosides and gangliosides. "Lipids" also include, but are not limited to, the common classes of glycerophospholipids (or phospholipids), such as phosphatidic acid, phosphatidylethanolamine, phosphatidylcholine, phosphatidylserine, phosphatidylinositol, phosphatidylglycerol, and the like.

As used herein, a "drug" can be a known drug or a drug candidate, whose activity or effects on a particular cell type are not yet known. A "drug metabolite" is any of the by-products or the breakdown products of a drug that is changed chemically into another compound or compounds. As used herein, "small organic molecule" includes, but is not limited to, an organic molecule or compound that does not fit precisely into other classifications highlighted herein. More particularly, the term "small organic molecule" as used herein, refers to organic compounds, whether naturally-occurring or artificially created (e.g., via chemical synthesis) that have relatively low molecular weight and that are not proteins, polypeptides, or nucleic acids. Typically, small molecules have a molecular weight of less than about 1500 g/mol. Also, small molecules typically have multiple carbon-carbon bonds.

As used herein, the term "sample" includes any liquid or fluid sample, including a sample derived from a biological source, such as a physiological fluid, including whole blood or whole blood components, such as red blood cells, white blood cells, platelets, serum and plasma; ascites; urine; saliva; sweat; milk; synovial fluid; peritoneal fluid; amniotic fluid; percerebrospinal fluid; lymph fluid; lung embolism; cerebrospinal fluid; pericardial fluid; cervicovaginal samples; tissue extracts; cell extracts; and other constituents of the body that are suspected of containing the analyte of interest. In addition to physiological fluids, other liquid samples, such as water, food products and the like, for the performance of environmental or food production assays are suitable for use with the presently disclosed subject matter. A solid material suspected of containing the analyte also can be used as the test sample. In some instances it might be beneficial to modify a solid test sample to form a liquid medium or to release the analyte.

In some embodiments, the sample can be pre-treated prior to use, such as preparing plasma from blood, diluting viscous fluids, or the like. Such methods of treatment can involve filtration, distillation, concentration, inactivation of interfering compounds, and the addition of reagents.

The sample can be any sample obtained from a subject. The term "subject" refers to an organism, tissue, or cell from which a sample can be obtained. A subject can include a human subject for medical purposes, such as diagnosis and/or treatment of a condition or disease, or an animal subject for medical, veterinary purposes, or developmental purposes. A subject also can include sample material from tissue culture, cell culture, organ replication, stem cell production and the like. Suitable animal subjects include mammals and avians. The term "avian" as used herein includes, but is not limited to, chickens, ducks, geese, quail, turkeys, and pheasants. The term "mammal" as used herein includes, but is not limited to, primates, e.g, humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. Preferably, the subject is a mammal or a mammalian cell. More preferably, the subject is a human or a human cell. Human subjects include, but are not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein. A subject also can refer to cells or collections of cells in laboratory or bioprocessing culture in tests for viability, differentiation, marker production, expression, and the like.

The presently disclosed methods can be used to diagnose, for the prognosis, or the monitoring of a disease state or condition. As used herein, the term "diagnosis" refers to a predictive process in which the presence, absence, severity or course of treatment of a disease, disorder or other medical condition is assessed. For purposes herein, diagnosis also includes predictive processes for determining the outcome resulting from a treatment. Likewise, the term "diagnosing," refers to the determination of whether a sample specimen exhibits one or more characteristics of a condition or disease. The term "diagnosing" includes establishing the presence or absence of, for example, a target antigen or reagent bound targets, or establishing, or otherwise determining one or more characteristics of a condition or disease, including type, grade, stage, or similar conditions. As used herein, the term "diagnosing" can include distinguishing one form of a disease from another. The term "diagnosing" encompasses the initial diagnosis or detection, prognosis, and monitoring of a condition or disease.

The term "prognosis," and derivations thereof, refers to the determination or prediction of the course of a disease or condition. The course of a disease or condition can be determined, for example, based on life expectancy or quality of life. "Prognosis" includes the determination of the time course of a disease or condition, with or without a treatment or treatments. In the instance where treatment(s) are contemplated, the prognosis includes determining the efficacy of a treatment for a disease or condition.

As used herein, the term "risk" refers to a predictive process in which the probability of a particular outcome is assessed.

The term "monitoring," such as in "monitoring the course of a disease or condition," refers to the ongoing diagnosis of samples obtained from a subject having or suspected of having a disease or condition.

The term "marker" refers to a molecule, such as a protein, including an antigen, that when detected in a sample is characteristic of or indicates the presence of a disease or condition.

The presently disclosed subject matter also provides methods for monitoring disease states in a subject, including chronic diseases, such as, but not limited to, diabetes, including Type 1 and Type 2 diabetes, heart disease, coronary artery disease, metabolic disorders, inflammatory diseases, such as rheumatoid arthritis, and cancer. The metabolic disorders can include, but are not limited to, hyperlipidemia, hypolipidemia, hyperthyroidism, and hypothyroidism.

Further, the presently disclosed methods can be used to monitor specific markers of a chronic disease. By monitoring the concentrations of molecular artifacts, metabolites, and deleterious and/or beneficial molecules of a disease state, the subject's progression, regression or stability can be assessed, and treatments can, in turn be adjusted or revised accordingly. For example, markers for heart disease that could be monitored using the presently disclosed biosensors include, but are not limited to, total fatty acids, lactate, glucose, free fatty acids and various cardiotonic agents, such as, but not limited to cardioglycosides and sympathomimetics.

Markers of diabetes include, but are not limited to, glucose, lactate and fatty acids. Likewise, markers for coronary artery disease include, but are not limited to, C-reactive peptide and free fatty acids. Generally, markers of various metabolic disorders include, but are not limited to, specific fatty acids.

The presently disclosed biosensor compounds also are suitable for use in devices for monitoring drug treatment. Indeed, the biosensor could be designed to specifically bind a drug, drug candidate or a drug metabolite. In this manner, the plasma concentration of the drug could be monitored and dosages could be adjusted or maintained based on the concentration measurements provided by the sensor. Accordingly, a pharmaceutical regimen could be individualized for a particular subject, including the use of a biosensor that can specifically and reversibly bind the drug or drug metabolite to determine plasma concentrations of the drug. The concentrations provided by the sensor can then be used to determine the bioavailability of the drug in the subject. The dose of the drug administered to the subject can then be altered to increase or decrease the bioavailability of the drug to the subject to provide maximum therapeutic benefits and avoiding toxicity.

Biosensor devices comprising the presently disclosed biosensor compounds can be used to simultaneously monitor a variety of metabolites, the measurements of which could be used to profile the subject's metabolic or physical state. For example, during extended periods of strenuous exercise, glucose is broken down in anaerobic processes to lactic acid. The presently disclosed biosensors can be used to determine lactate thresholds of athletes, to maximize the benefits of training and decrease recovery time. Similarly, the biosensors can be used to determine lactate thresholds in soldiers to prevent fatigue and exhaustion and to decrease recovery time. To that end, the presently disclosed biosensors can be used to monitor glucose levels, lactic acids levels and other metabolites during exercise or physical stress.

III. Biosensor Devices, Reagents, and Kits Including Biosensor Compounds of Formula (I-IV)

A. Biosensor Devices Including Compounds of Formula (I-IV)

In some embodiments, the presently disclosed biosensor compounds can be included in a biosensor device that is capable of conveying a signal, e.g., a signal related to the absorption spectrum or change in the absorption spectrum of the environmentally-sensitive dye, to a detector that is capable of detecting the signal. In some embodiments, the device comprises the detector, whereas in other embodiments, the device does not comprise the detector, i.e., the detector is external to the device. The signal generated by the device can be a direct indicator of the binding of the one or more target analytes to the binding member, e.g., a binding protein or receptor, associated with the dye.

Accordingly, in some embodiments, the presently disclosed subject matter provides a glucose sensor device comprising a biosensor compound of Formula (I-IV):

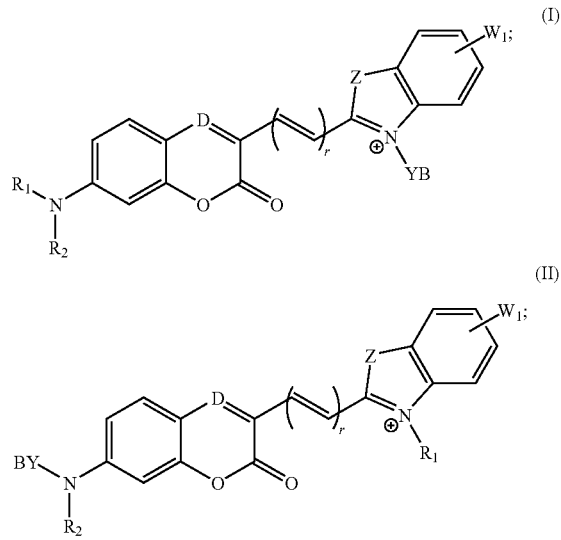

-continued

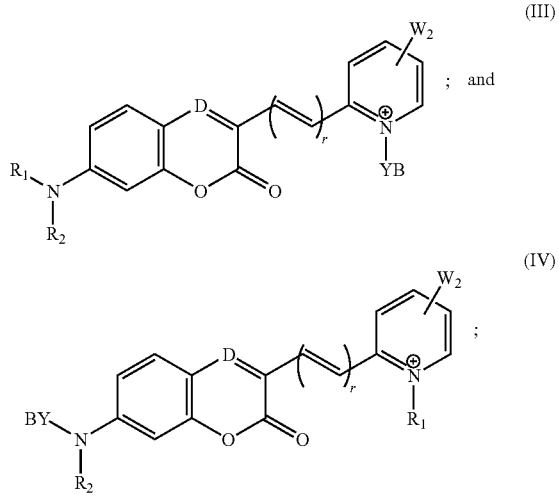

wherein:
r is an integer from 1 to 8;
D is CH or N;
$R_1$ and $R_2$ are each independently selected from the group consisting of alkyl, substituted alkyl, and $(CH_2)_sCO_2H$, wherein s is an integer from 2 to 5;
Z is selected from the group consisting of S, O, and —$CR_3R_4$, wherein $R_3$ and $R_4$ are each independently alkyl or substituted alkyl;
$W_1$ is selected from the group consisting of H, alkyl, substituted alkyl, $SO_3H$, fused benzene, and fused sulfobenzene;
$W_2$ is selected from the group consisting of H, alkyl, substituted alkyl, $SO_3H$, heteroalkyl, substituted heteroalkyl, cycloalkyl, substituted cycloalkyl, cycloheteroalkyl, substituted cycloheteroalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl;
Y—B is selected from the group consisting of:
—$(CH_2)_nX_1C(=O)$—$(CH_2)_m$—B,

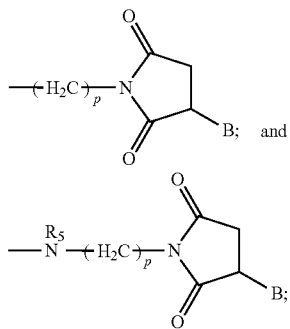

wherein:
m, n, and p are each independently an integer from 1 to 8;
$X_1$ is O or $NR_6$;
$R_5$ and $R_6$ are each independently selected from the group consisting of H, alkyl, substituted alkyl, heteroalkyl, substituted heteroalkyl, cycloalkyl, substituted cycloalkyl, cycloheteroalkyl, substituted cycloheteroalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; and B is a glucose/galactose binding protein (GGBP) or a mutated GGBP; and
wherein the biosensor compound exhibits a detectable color change as a result of binding to glucose or as a result of a change in concentration of the glucose in the sample.

In some embodiments, the presently disclosed glucose sensor device comprises a biosensor compound has a structure selected from the group consisting of:

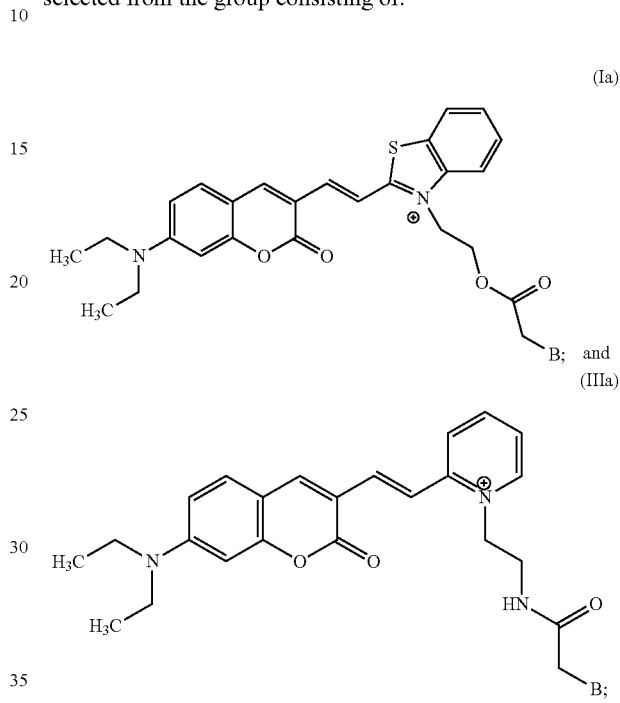

wherein B is a glucose/galactose binding protein (GGBP) or a mutated GGBP. In some embodiments, the mutated GGBP is selected from the group consisting of W183C, SM4, and Y10C. In some embodiments, the mutated GGBP is W183C. In other embodiments, the mutated GGBP is SM4.

The presently disclosed biosensor compounds can be used in biosensor devices suitable for use in various settings. Such devices include medical devices for monitoring metabolic substrate levels in a subject. Exemplary biosensor devices, include, but are not limited to, biosensor devices described in copending U.S. application Ser. No. 11/738,442, filed Apr. 20, 2007, U.S. Patent Application Publication No. 2006/0078908, to Pitner et al., filed Jun. 7, 2005, U.S. Pat. No. 6,922,576 to Raskas, issued Jul. 26, 2005, integrated delivery and monitoring devices, such as those described in U.S. Pat. No. 6,192,891 to Gravel et al., issued Feb. 27, 2001, U.S. Pat. No. 3,964,871, to Hochstrasser, issued Jun. 22, 1976, U.S. Patent Application Publication No. 2005/0113658, to Jacobson et al., filed Oct. 19, 2004, U.S. Patent Application Publication No. 2005/0240119 to Draudt et al., filed Apr. 15, 2005, each of which are incorporated by reference in their entirety, and wherein such devices, or components thereof, are adapted for detecting a color change in the presently disclosed biosensor compounds in the presence of a target analyte or ligand, such as glucose.

Biosensor devices comprising the presently disclosed biosensor compounds can be used to monitor a condition or disease state in a patient in an acute care facility, such as an emergency room or a post-operative recovery room or a hospital. For example, in embodiments providing a method for monitoring glucose levels in a subject, studies have shown that mortality can be decreased by as much as 30% in post-operative patients when glucose levels are monitored and kept normal. Thus, the presently disclosed biosensor can be used in situations where monitoring glucose or other metabolites is essential to recovery or the overall health of the subject.

The presently disclosed biosensor can be used or adapted for use in strips, implants, micro- and nano-particles, and the like. More particularly, in some embodiments, the presently disclosed sensor can be immobilized on a solid matrix, for example, a chromatographic test strip.

B. Reagents Including Compounds of Formula (I-IV)

In some embodiments, the presently disclosed subject matter provides a reagent for determining the presence or amount of glucose in a sample, the reagent comprising a biosensor compound of Formula (I-IV):

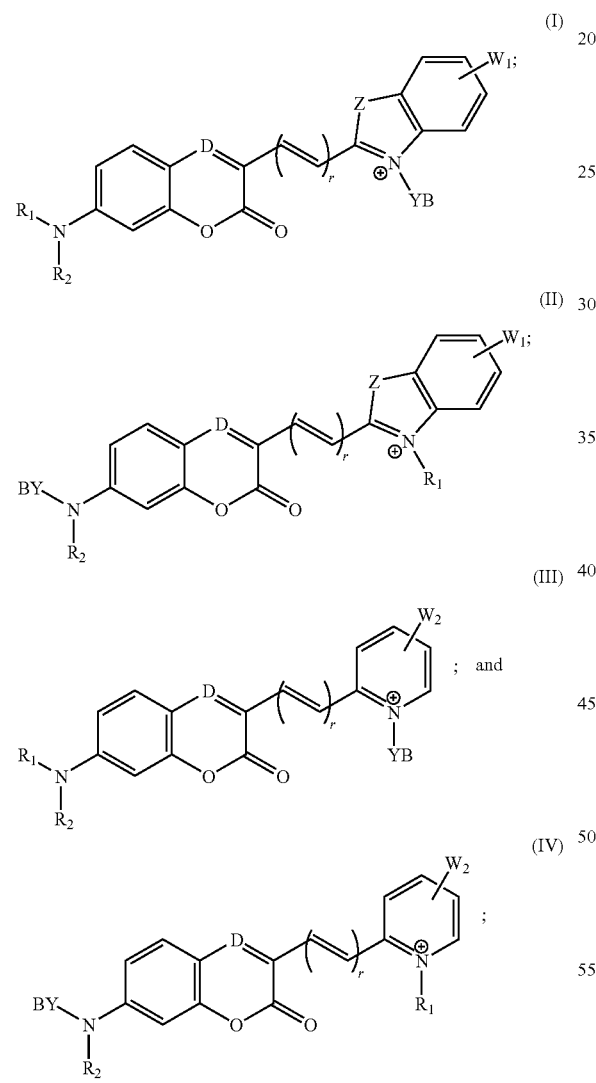

wherein:
r is an integer from 1 to 8;
D is CH or N;
$R_1$ and $R_2$ are each independently selected from the group consisting of alkyl, substituted alkyl, and $(CH_2)_sCO_2H$, wherein s is an integer from 2 to 5;

Z is selected from the group consisting of S, O, and $-CR_3R_4$, wherein $R_3$ and $R_4$ are each independently alkyl or substituted alkyl;

$W_1$ is selected from the group consisting of H, alkyl, substituted alkyl, $SO_3H$, fused benzene, and fused sulfobenzene;

$W_2$ is selected from the group consisting of H, alkyl, substituted alkyl, $SO_3H$, heteroalkyl, substituted heteroalkyl, cycloalkyl, substituted cycloalkyl, cycloheteroalkyl, substituted cycloheteroalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl;

Y—B is selected from the group consisting of:

$-(CH_2)_nX_1C(=O)-(CH_2)_m-B$,

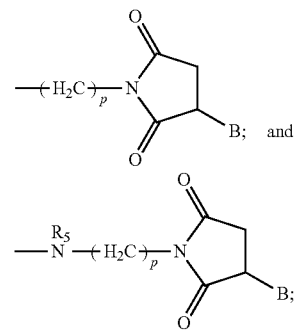

wherein:
m, n, and p are each independently an integer from 1 to 8;
$X_1$ is O or $NR_6$;
$R_5$ and $R_6$ are each independently selected from the group consisting of H, alkyl, substituted alkyl, heteroalkyl, substituted heteroalkyl, cycloalkyl, substituted cycloalkyl, cycloheteroalkyl, substituted cycloheteroalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; and B is a glucose/galactose binding protein (GGBP) or a mutated GGBP; and wherein the biosensor compound exhibits a detectable color change as a result of binding to glucose or as a result of a change in concentration of the glucose in the sample.

C. Kits Including Compounds of Formula (I-IV)

In some embodiments, the presently disclosed subject matter provides a kit for determining the presence or amount of glucose in a sample, the kit comprising a biosensor compound of Formula (I-IV):

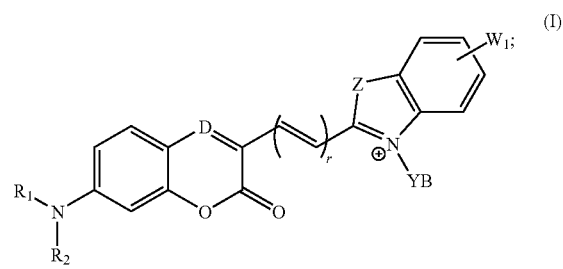

-continued

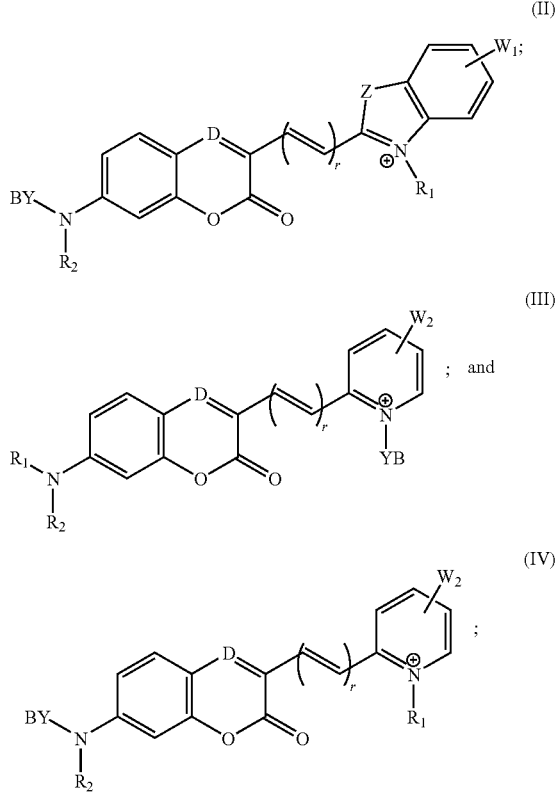

wherein:
r is an integer from 1 to 8;
D is CH or N;
R$_1$ and R$_2$ are each independently selected from the group consisting of alkyl, substituted alkyl, and (CH$_2$)$_s$CO$_2$H, wherein s is an integer from 2 to 5;
Z is selected from the group consisting of S, O, and —CR$_3$R$_4$, wherein R$_3$ and R$_4$ are each independently alkyl or substituted alkyl;
W$_1$ is selected from the group consisting of H, alkyl, substituted alkyl, SO$_3$H, fused benzene, and fused sulfobenzene;
W$_2$ is selected from the group consisting of H, alkyl, substituted alkyl, SO$_3$H, heteroalkyl, substituted heteroalkyl, cycloalkyl, substituted cycloalkyl, cycloheteroalkyl, substituted cycloheteroalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl;
Y—B is selected from the group consisting of:
—(CH$_2$)$_n$X$_1$C(═O)—(CH$_2$)$_m$—B,

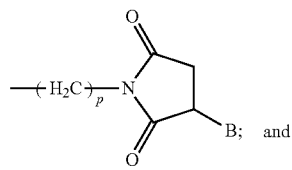

wherein:
m, n, and p are each independently an integer from 1 to 8;
X$_1$ is O or NR$_6$;
R$_5$ and R$_6$ are each independently selected from the group consisting of H, alkyl, substituted alkyl, heteroalkyl, substituted heteroalkyl, cycloalkyl, substituted cycloalkyl, cycloheteroalkyl, substituted cycloheteroalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; and
B is a glucose/galactose binding protein (GGBP) or a mutated GGBP; and
wherein the biosensor compound exhibits a detectable color change as a result of binding to glucose or as a result of a change in concentration of the glucose in the sample.

IV. Chemical Definitions

While the following terms are believed to be well understood by one of ordinary skill in the art, the following definitions are set forth to facilitate explanation of the presently disclosed subject matter. Unless otherwise defined, all technical and scientific terms used herein have the same meaning as commonly understood by one of ordinary skill in the art to which this presently described subject matter belongs.

Throughout the specification and claims, a given chemical formula or name shall encompass all optical and stereoisomers, as well as racemic mixtures where such isomers and mixtures exist.

When the term "independently selected" is used, the substituents being referred to (e.g., R groups, such as groups R$_1$, R$_2$, and the like, or groups X$_1$ and X$_2$), can be identical or different. For example, both R$_1$ and R$_2$ can be substituted alkyls, or R$_1$ can be hydrogen and R$_2$ can be a substituted alkyl, and the like.

A named "R" or "X" group will generally have the structure that is recognized in the art as corresponding to a group having that name, unless specified otherwise herein. For the purposes of illustration, certain representative "R" and "X" groups as set forth above are defined below. These definitions are intended to supplement and illustrate, not preclude, the definitions that would be apparent to one of ordinary skill in the art upon review of the present disclosure.

As used herein the term "alkyl" refers to C$_{1-20}$ inclusive, linear (i.e., "straight-chain"), branched, or cyclic, saturated or at least partially and in some cases fully unsaturated (i.e., alkenyl and alkynyl)hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a C$_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl.

The term "cycloalkylalkyl," as used herein, refers to a cycloalkyl group as defined hereinabove, which is attached to the parent molecular moiety through an alkyl group, also as defined above. Examples of cycloalkylalkyl groups include cyclopropylmethyl and cyclopentylethyl.

The terms "cycloheteroalkyl" or "heterocycloalkyl" refer to a non-aromatic ring system, such as a 3- to 7-member substituted or unsubstituted cycloalkyl ring system, including one or more heteroatoms, which can be the same or different, and are selected from the group consisting of N, O, and S, and optionally can include one or more double bonds. The cycloheteroalkyl ring can be optionally fused to or otherwise attached to other cycloheteroalkyl rings and/or non-aromatic hydrocarbon rings. Representative cycloheteroalkyl ring systems include, but are not limited to pyrrolidinyl, pyrrolinyl, imidazolidinyl, imidazolinyl, pyrazolidinyl, pyrazolinyl, piperidyl, piperazinyl, indolinyl, quinuclidinyl, morpholinyl, thiomorpholinyl, thiadiazinanyl, tetrahydrofuranyl, and the like.

The term "alkenyl" as used herein refers to a straight or branched hydrocarbon of a designed number of carbon atoms containing at least one carbon-carbon double bond. Examples of "alkenyl" include vinyl, allyl, 2-methyl-3-heptene, and the like.

The term "cycloalkenyl" as used herein refers to a cyclic hydrocarbon containing at least one carbon-carbon double bond. Examples of cycloalkenyl groups include cyclopropenyl, cyclobutenyl, cyclopentenyl, cyclopentadiene, cyclohexenyl, 1,3-cyclohexadiene, cycloheptenyl, cycloheptatrienyl, and cyclooctenyl.

The term "alkynyl" as used herein refers to a straight or branched hydrocarbon of a designed number of carbon atoms containing at least one carbon-carbon triple bond. Examples of "alkynyl" include propargyl, propyne, and 3-hexyne.

"Alkylene" refers to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—$CH_2$—); ethylene (—$CH_2$—$CH_2$—); propylene (—$(CH_2)_3$—); cyclohexylene (—$C_6H_{10}$—); —CH=CH—CH=CH—; —CH=CH—$CH_2$—; —$(CH_2)_q$—N(R)—$(CH_2)_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—$CH_2$—O—); and ethylenedioxyl (—O—$(CH_2)_2$—O—). An alkylene group can have about 2 to about 3 carbon atoms and can further have 6-20 carbons.

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

The term "heteroaryl" refers to an aromatic ring system, such as, but not limited to a 5- or 6-member ring system, including one or more heteroatoms, which can be the same or different, and are selected from the group consisting of N, O, and S. The heteroaryl ring can be fused or otherwise attached to one or more heteroaryl rings, aromatic or non-aromatic hydrocarbon rings, or heterocycloalkyl rings. Representative heteroaryl ring systems include, but are not limited to, pyridyl, pyrimidyl, pyrrolyl, pyrazolyl, azolyl, oxazolyl, isoxazolyl, oxadiazolyl, thiazolyl, isothiazolyl, imidazolyl, furanyl, thienyl, quinolinyl, isoquinolinyl, indolinyl, indolyl, benzothienyl, benzothiazolyl, enzofuranyl, benzimidazolyl, benzisoxazolyl, benzopyrazolyl, triazolyl, tetrazolyl, and the like.

A structure represented generally by the formula, wherein the ring structure can be aromatic or non-aromatic:

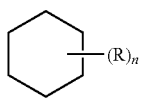

as used herein refers to a ring structure, for example, but not limited to a 3-carbon, a 4-carbon, a 5-carbon, a 6-carbon, and the like, aliphatic and/or aromatic cyclic compound, including a saturated ring structure, a partially saturated ring structure, and an unsaturated ring structure as defined herein, comprising a substituent R group, wherein the R group can be present or absent, and when present, one or more R groups can each be substituted on one or more available carbon atoms of the ring structure. The presence or absence of the R group and number of R groups is determined by the value of the integer n. Each R group, if more than one, is substituted on an available carbon of the ring structure rather than on another R group. For example, the structure above where n is 0 to 2 would comprise compound groups including, but not limited to:

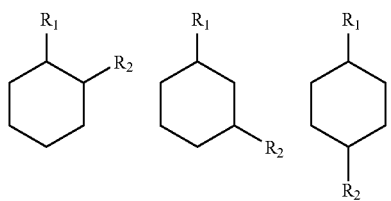

and the like.

A dashed line representing a bond in a cyclic ring structure indicates that the bond can be either present or absent in the ring. That is, a dashed line representing a bond in a cyclic ring structure indicates that the ring structure is selected from the group consisting of a saturated ring structure, a partially saturated ring structure, and an unsaturated ring structure.

When a named atom of an aromatic ring or a heterocyclic aromatic ring is defined as being "absent," the named atom is replaced by a direct bond.

As used herein, the term "acyl" refers to an organic acid group wherein the —OH of the carboxyl group has been replaced with another substituent (i.e., as represented by RCO—, wherein R is an alkyl or an aryl group as defined herein). As such, the term "acyl" specifically includes arylacyl groups, such as an acetylfuran and a phenacyl group. Specific examples of acyl groups include acetyl and benzoyl.

"Alkoxyl" refers to an alkyl-O— group wherein alkyl is as previously described. The term "alkoxyl" as used herein can refer to $C_{1-20}$ inclusive, linear, branched, or cyclic, saturated or unsaturated oxo-hydrocarbon chains, including, for example, methoxyl, ethoxyl, propoxyl, isopropoxyl, butoxyl, t-butoxyl, and pentoxyl.

The term "alkoxyalkyl" as used herein refers to an alkyl-O-alkyl ether, for example, a methoxyethyl or an ethoxymethyl group.

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

The term "alkyl-thio-alkyl" as used herein refers to an alkyl-S-alkyl thioether, for example, a methylthiomethyl or a methylthioethyl group.

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl.

"Alkoxycarbonyl" refers to an alkyl-O—CO— group. Exemplary alkoxycarbonyl groups include methoxycarbonyl, ethoxycarbonyl, butyloxycarbonyl, and t-butyloxycarbonyl. "Aryloxycarbonyl" refers to an aryl-O—CO— group. Exemplary aryloxycarbonyl groups include phenoxy- and naphthoxy-carbonyl. "Aralkoxycarbonyl" refers to an aralkyl-O—CO— group. An exemplary aralkoxycarbonyl group is benzyloxycarbonyl.

"Carbamoyl" refers to an $H_2N$—CO— group. "Alkylcarbamoyl" refers to a R'RN—CO— group wherein one of R and R' is hydrogen and the other of R and R' is alkyl and/or substituted alkyl as previously described. "Dialkylcarbamoyl" refers to a R'RN—CO— group wherein each of R and R' is independently alkyl and/or substituted alkyl as previously described.

"Acyloxyl" refers to an acyl-O— group wherein acyl is as previously described.

The term "amino" refers to the —$NH_2$ group and also refers to a nitrogen containing group as is known in the art derived from ammonia by the replacement of one or more hydrogen radicals by organic radicals. For example, the terms "acylamino" and "alkylamino" refer to specific N-substituted organic radicals with acyl and alkyl substituent groups respectively.

The term "alkylamino" refers to an —NHR group wherein R is an alkyl group and/or a substituted alkyl group as previously described. Exemplary alkylamino groups include methylamino, ethylamino, and the like.

"Dialkylamino" refers to an —NRR' group wherein each of R and R' is independently an alkyl group and/or a substituted alkyl group as previously described. Exemplary dialkylamino groups include ethylmethylamino, dimethylamino, and diethylamino.

"Acylamino" refers to an acyl-NH— group wherein acyl is as previously described. "Aroylamino" refers to an aroyl-NH— group wherein aroyl is as previously described.

The term "carbonyl" refers to the —(C=O)— group.
The term "carboxyl" refers to the —COOH group.
The terms "halo", "halide", or "halogen" as used herein refer to fluoro, chloro, bromo, and iodo groups.
The term "hydroxyl" refers to the —OH group.
The term "hydroxyalkyl" refers to an alkyl group substituted with an —OH group.
The term "mercapto" refers to the —SH group.
The term "oxo" refers to a compound described previously herein wherein a carbon atom is replaced by an oxygen atom.

The term "nitro" refers to the —$NO_2$ group.

The term "thio" refers to a compound described previously herein wherein a carbon or oxygen atom is replaced by a sulfur atom.

The term "sulfate" refers to the —$SO_4$ group.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The following Examples are offered by way of illustration and not by way of limitation.

Example 1

The GGBP mutant W183C was prepared by Paragon Biosciences, Baltimore Md. The labeling of the dye to the protein can be carried out as follows: about 0.8 mg of the lyophilized protein is dissolved in 0.4 mL of phosphate buffered saline (PBS) (pH of 7.4) and then treated with 15 μL of 2-mM dithiothreitol (DTT) for 30 minutes. One (1) mg of the dye, e.g., a dye molecule as represented in a biosensor compound of Formula Ia, is dissolved in 100 μL of dimethyl sulfoxide (DMSO) and 15 μL of this solution is added to the reaction mixture and kept in the dark for four (4) hours. The dye labeled protein can be separated by size exclusion chromatography using a NAP5 column. 100 μL of this solution is treated with 10 μL of 1M glucose solution leading to a final glucose concentration of 100 mM.

Under these conditions, the color of the solution instantaneously changed from magenta to blue. FIG. 1 shows representative absorption spectra of the dye before the addition of glucose and after the addition of glucose. The absorption maximum of the dye before the addition of glucose was centered at about 550 nm. The absorption maximum shifted to about 590 nm after the addition of 100 mM glucose.

Example 2

The presently disclosed biosensor compounds can exhibit a change in absorption spectrum in the presence of glucose. For example, FIG. 2 shows a change in representative absorption spectra of a biosensor compound of Formula (IIIa), e.g., SM4-o-ICOPIC, with increasing glucose concentration over the glucose concentration range of about 0 mM to about 100 mM. Further, the glucose binding range of the presently disclosed biosensor compounds falls within the human physiological range of glucose (Kd=15 mM). See FIG. 3, which shows a representative ratiometric glucose binding curve obtained from absorption spectra of a biosensor compound of Formula (IIIa), e.g., SM4-o-ICOPIC, over glucose concentrations ranging from about 0 mM to about 100 mM.

Example 3

The change in absorption spectra upon binding glucose also provides the opportunity to excite the protein-dye system at different wavelengths to produce variations in the observed fluorescence spectra. The changes in the fluorescence spectra provide the ability to tailor calibration parameters and other instrumentation-based data analysis. See, for example, FIGS. 4A-4D, which show the effect of excitation wavelength on the fluorescence spectra of a biosensor compound of Formula (IIIa), e.g., SM4-o-ICOPIC, at excitation wavelengths of 485 nm, 495 nm, 505 nm, and 515 nm, respectively.

Example 4

Values illustrating the effect of excitation wavelength on Kd and QR* are provided in Table 1.

TABLE 1

Effect of Excitation Wavelength on Binding Parameters

| Type | Excitation Wavelength (λ nm) | Ratio | Blue (λ nm) | Green (λ nm) | $^{app}Kd$ (mM) | QR* |
|---|---|---|---|---|---|---|
| Abs | NA | Green/Blue | 425-470 | 515-600 | 15.6 | 4.4 |
| Fluor | 485 | Blue/Green | 560-580 | 650-670 | 8.0 | 5.6 |
| Fluor | 495 | Blue/Green | 560-580 | 650-670 | 7.1 | 5.9 |
| Fluor | 505 | Blue/Green | 560-580 | 650-670 | 6.0 | 6.3 |
| Fluor | 515 | Blue/Green | 560-580 | 650-670 | 4.9 | 6.6 |

Kd and QR* values obtained from the equation "Ratio = $R_{inf}$ * [Glc] + $R_0$ * Kd)/(Kd + [Glc])", where QR* = $R_0/R_{inf}$, except for the absorbance where QR* = $R_{inf}/R_0$.

All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

The references listed below, as well as all references cited in the specification, are incorporated herein by reference to the extent that they supplement, explain, provide a background for or teach methodology, techniques and/or compositions employed herein.

Alexeev, V., et al., Photonic Crystal Glucose-Sensing Material for Noninvasive Monitoring of Glucose in Tear Fluid," *Clinical Chemistry*, 50:2353 (2004).

Long, J., et al., *J. Heterocyclic Chem.*, 36:895-899 (1999).

U.S. Pat. No. 6,277,627 to Hellinga, issued Aug. 21, 2001.

U.S. Pat. No. 6,855,556 to Amiss et al., issued Feb. 15, 2005.

U.S. Published Patent Application No. 2006/0280652 to Pitner et al., for Long Wavelength Thiol Reactive Fluorophores, filed May 18, 2005.

U.S. Published Patent Application No. 2005/0042704 to Alarcon et al., for Entrapped Binding Protein as Biosensors, filed Sep. 27, 2004.

U.S. Published Patent Application No. 2005/0014290 to Hsieh et al., for Binding Protein as Biosensors, filed Feb. 12, 2004.

Although the foregoing subject matter has been described in some detail by way of illustration and example for purposes of clarity of understanding, it will be understood by those skilled in the art that certain changes and modifications can be practiced within the scope of the appended claims.

What is claimed is:

1. A method for determining the presence or amount of glucose in a sample, the method comprising:
   (a) providing a biosensor compound of Formula III or IV:

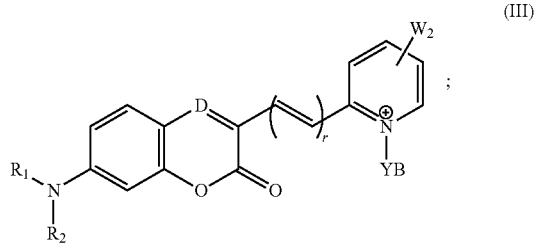

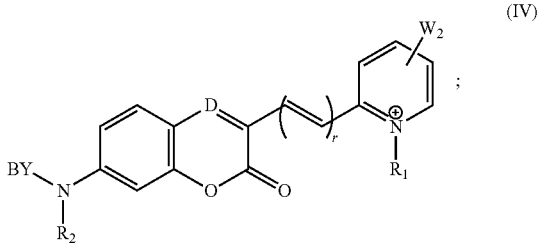

wherein:
r is an integer from 1 to 8;
D is CH or N;
$R_1$ and $R_2$ are each independently selected from the group consisting of alkyl, substituted alkyl, and $(CH_2)_sCO_2H$, wherein s is an integer from 2 to 5;
$W_2$ is selected from the group consisting of H, alkyl, substituted alkyl, $SO_3H$, heteroalkyl, substituted heteroalkyl, cycloalkyl, substituted cycloalkyl, cycloheteroalkyl, substituted cycloheteroalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl;
Y—B is selected from the group consisting of:
—$(CH_2)_nX_1C(=O)$—$(CH_2)_m$—B,

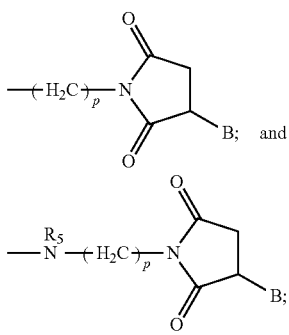

wherein:
m, n, and p are each independently an integer from 1 to 8;
$X_1$ is O or $NR_6$;
$R_5$ and $R_6$ are each independently selected from the group consisting of H, alkyl, substituted alkyl, heteroalkyl, substituted heteroalkyl, cycloalkyl, substituted cycloalkyl, cycloheteroalkyl, substituted cycloheteroalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; and
B is mutated glucose/galactose binding protein (GGBP) having a binding affinity for glucose; and
   wherein the biosensor compound exhibits a detectable color change within the visible spectrum as a result of binding to glucose or as a result of a change in concentration of glucose in the sample;
   (b) contacting the biosensor compound with a sample suspected of containing glucose to bind the glucose, if present, to the binding protein; and
   (c) visually observing a color change, wherein the color change is a visible result of a shift of at least 30 nm in the absorption wavelength of the biosensor compound in the presence of glucose, to determine the presence or amount of glucose in the sample.

2. The method of claim 1, wherein the biosensor compound is:

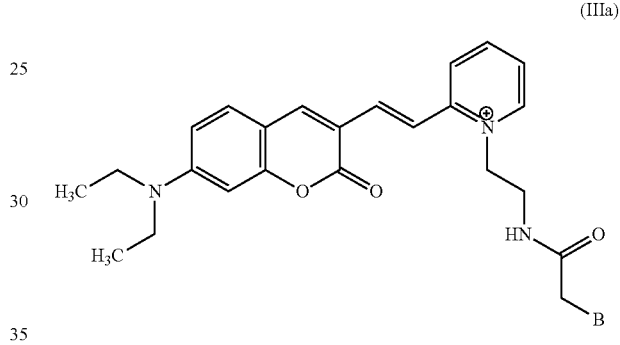

3. The method of claim 1, wherein the mutated GGBP is selected from the group consisting of W183C, SM4, and Y10C wherein SM4 is mutated glucose/galactose binding protein (GGBP) having the following substitutions: N39I, G82E, Q83K, N84D, Q175E, Q177H, L178M, W183C, N259E and N260S.

4. The method of claim 2, wherein the mutated GGBP is W183C.

5. The method of claim 2, wherein the mutated GGBP is SM4.

6. The method of claim 1, further comprising continuously:
   (a) contacting the mutated GGBP with the sample suspected of containing glucose; and
   (b) visually observing the color change.

7. The method of claim 1, wherein the mutated GGBP undergoes a conformation change as a result of a change in glucose concentration of the sample suspected of containing glucose and wherein the method provides a visual change in color as a result of the change in the glucose concentration.

8. The method of claim 1, wherein the biosensor compound of Formula III or IV is immobilized on a solid matrix.

9. The method of claim 8, wherein the solid matrix comprises a chromatographic test strip.

10. The method of claim 1, wherein the color change includes a change from a first absorption wavelength of about 550 nm before the biosensor compound is contacted with the sample suspected of containing glucose to a second absorption wavelength of about 590 nm after the biosensor compound is contacted with the sample suspected of containing glucose.

11. The method of claim 1, wherein the color change includes a change from a first absorption wavelength of about 490 nm before the biosensor compound is contacted with the sample suspected of containing glucose to a second absorption wavelength of about 520 nm after the biosensor compound is contacted with the sample suspected of containing glucose.

12. The method of claim 1, wherein the detecting of the color change comprises comparing an absorption wavelength or an intensity of an absorption wavelength of the biosensor compound with a color wheel.

13. The method of claim 2, wherein the biosensor compound is a compound of Formula (IIIa) and B is SM4, wherein SM4 is mutated glucose/galactose binding protein (GGBP) having the following substitutions: N39I, G82E, Q83K, N84D, Q175E, Q177H, L178M, W183C, N259E and N260S.

* * * * *